United States Patent
Qiu et al.

(10) Patent No.: US 12,077,602 B2
(45) Date of Patent: Sep. 3, 2024

(54) IgG EPITOPE AND APPLICATIONS THEREOF AS A DRUG TARGET

(71) Applicant: Beijing SIG Biopharmaceutical Technology Co., Ltd., Beijing (CN)

(72) Inventors: Xiaoyan Qiu, Beijing (CN); Jingshu Tang, Beijing (CN); Zhi Yang, Beijing (CN); Chong Wang, Beijing (CN); Jingxuan Zhang, Beijing (CN); Hua Zhu, Beijing (CN); Zihan Geng, Beijing (CN); Yang Liu, Beijing (CN); Wenhua Jiang, Beijing (CN); Jing Huang, Beijing (CN)

(73) Assignee: Beijing SIG Biopharmaceutical Technology Co., Ltd., Beijing (CN)

( * ) Notice: Subject to any disclaimer, the term of this patent is extended or adjusted under 35 U.S.C. 154(b) by 294 days.

(21) Appl. No.: 16/969,189

(22) PCT Filed: Aug. 8, 2018

(86) PCT No.: PCT/CN2018/099279
§ 371 (c)(1),
(2) Date: Aug. 11, 2020

(87) PCT Pub. No.: WO2019/153674
PCT Pub. Date: Aug. 15, 2019

(65) Prior Publication Data
US 2020/0369785 A1    Nov. 26, 2020

(30) Foreign Application Priority Data

Feb. 12, 2018  (CN) .......................... 201810146884.X
Apr. 13, 2018  (CN) .......................... 201810330585.1

(51) Int. Cl.
*C07K 16/42*    (2006.01)
*G01N 33/68*    (2006.01)

(52) U.S. Cl.
CPC ..... *C07K 16/4283* (2013.01); *G01N 33/6854* (2013.01); *C07K 2317/41* (2013.01); *C07K 2317/522* (2013.01); *G01N 2333/70546* (2013.01); *G01N 2333/91148* (2013.01)

(58) Field of Classification Search
CPC ............ C07K 16/4283; C07K 2317/41; C07K 2317/522; G01N 33/6854
See application file for complete search history.

(56) References Cited

U.S. PATENT DOCUMENTS 8,974,786 B2 *  3/2015  Lee .......................... C07K 16/30
424/174.1

FOREIGN PATENT DOCUMENTS

CN    102901817 A    1/2013
CN    108610414 A    10/2018

OTHER PUBLICATIONS

Bierie et al., Integrin-β4 identifies cancer stem cell-enriched populations of partially mesenchymal carcinoma cells, PNAS, 2017, E2337-E2346, Publication Date: Mar. 7, 2017 (Year: 2017).*
Gura, T., Systems for Identifying New Drugs Are Often Faulty, Science, 1997, 278:1041-10 (Year: 1997).*
Kaiser, J., First pass at cancer genome reveals complex landscape, Science, 2006, 313:1370 (Year: 2006).*
Gerdes et al. Emerging understanding of multiscale tumor heterogeneity, Front. Oncol. Dec. 18, 2014 doi: 10.3389/fonc.2014.00366, pp. 1-12 (Year: 2014).*
Lee, CA215, A New Pan Cancer Biomarker, and its Clinical Applications, Cancer Sci Res Open Access 2(2): 1-6, Publication Date: Sep. 20, 2015 (Year: 2015).*
Lee, CA215 and GnRH receptor as targets for cancer therapy, Cancer Immunol Immunother, 2012, 61:1805-1817, Publication Date: Mar. 21, 2012 (Year: 2012).*
Herbert et al. The Dictionary of Immunology, Academic Press, 4th edition, 1995, p. 58 (Year: 1995).*
Greenspan et al., Defining epitopes is not as easy as it seems, Nature Biotechnology 7:936-937 (Year: 1999).*
Almagro & Fransson, Humanization of antibodies, Frontiers in Bioscience 2008; 13: 1619-33 (Year: 2008).*
Rudikoff et al., Single amino acid substitution altering antigen-binding specificity, PNAS, USA, 1982, 79: 1979-1983 (Year: 1982).*
Riemer et al., Matching of trastuzumab (Herceptin®) epitope mimics onto the surface of Her-2/neu—a new method of epitope definition, Mol Immunol, 2005 42(9): 1121-1124 (Year: 2005).*
Sela-Culang et al., The structural basis of antibody-antigen recognition, Frontiers in Immunology, vol. 4, article 302, Publication Date: Oct. 8, 2013 (Year: 2013).*
Harlow et al., Antibodies, A Laboratory Manual, Chapter 5, p. 76, 1988 (Year: 1988).*
SK-MES-1 cells at ATCC downloaded from https://www.atcc.org/products/htb-58. (Year: 2023).*
Jingshu Tang et al., Lung squamous cell carcinoma cells express non-canonically glycosylated IgG that activates integrin-FAK signaling, Cancer Letters, 2018, pp. 148-159, 430.

(Continued)

*Primary Examiner* — Peter J Reddig
*Assistant Examiner* — Cheng Lu
(74) *Attorney, Agent, or Firm* — Bayramoglu Law Offices

(57) ABSTRACT

IgG epitope and applications thereof as a target are provided. The IgG epitope is the $C_H1$ domain of non-B cell-derived IgG, and there is N-glycosylated sialic acid modification at the Asn162 site of the domain. The realization of its antigen functions must depend on the sialylation of the site. The present invention further discloses the applications of the IgG epitope as a drug target in preparing drugs for diagnosis and/or treatment of epithelial tumors. In addition, our studies showed that this antigen depends on the sialylation of Asn162 site as a drug target, and the sialylation of this site must depend on sialyltransferase ST3GAL4, indicating that the enzyme can be used as a drug target for preparing tumor therapeutic drugs. Further, integrin β4 is co-expressed and co-localized with IgG containing the epitope. IgG can be used as a marker for preparing drugs for the auxiliary detection of epithelial tumors.

4 Claims, 28 Drawing Sheets

Specification includes a Sequence Listing.

(56) References Cited

OTHER PUBLICATIONS

John F. Valliere-Douglass et al., Asparagine-linked Oligosaccharides Present on a Non-consensus Amino Acid Sequence in the CH1 Domain of Human Antibodies, Journal of Biological Chemistry, Nov. 20, 2009, pp. 32493-32506, vol. 284, No. 47.
Zhang Ying et al., Detection of the Expression of Integrin B4 in Epithelial Ovarian Tumor Tissues, Journal of Guiyang Medical College, 2009, pp. 12-15, vol. 34, No. 1.
Alessandro Natoni et al., Targeting Selectins and Their Ligands in Cancer, Frontiers in Oncology, Apr. 2016, pp. 1-12, vol. 6, Article 93.
Yang Liu et al., Binding of the monoclonal antibody RP215 to immunoglobulin G in metastatic lung adenocarcinomas is correlated with poor prognosis, John Wiley&Sons Ltd, Histopathology, 2015, pp. 1-9.
Chen Xi-Xi et al., The Role of Glycosyltransferase Superfamily in Tumor Metastasis, Progress in Biochemistry and Biophysics, 2017, pp. 877-887, vol. 44, No. 10.

\* cited by examiner

```
                    C_H1 mutation
150  KDYFPEPVTV SWNSGALTSG VHTFPAVLQS SGLYSLSSVV TVPSSNFGTQ TYTCHVDHKP
     KDYFPEPVTV AWCSGALTSG VHTFPAVLQS SGLYSLSSVV TVPSSNFGTQ TYTCHVDHKP
     KDYFPEPVTV SWNSGALTSG VHTFPAVLQS SGLYSLSSVV TVPSSNFGTQ TYTCHVDHKP 210  SNTKVDKTVE RKCCVECPPC PAPPVAGPSV FLFPPKPKDT LMISRTPEVT CVVVDVSHED
     SNTKVDKTVE RKCCVECPPC PAPPVAGPSV FLFPPKPKDT LMISRTPEVT CVVVDVSHED
     SNTKVDKTVE RKCCVECPPC PAPPVAGPSV FLFPPKPKDT LMISRTPEVT CVVVDVSHED PEVQFNWYVD GVEVHNAKTK PREEQFNSTF RVVSVLTVVH QDWLNGKEYK  WT
270  PEVQFNWYVD GVEVHNAKTK PREEQFNSTF RVVSVLTVVH QDWLNGKEYK  C_H1mu
     PEVQFNWYVD GVEVHNAKTK PREEQFQSTF RVVSVLTVVH QDWLNGKEYK  C_H2mu
                                C_H2 mutation
```

FIG. 1-2A

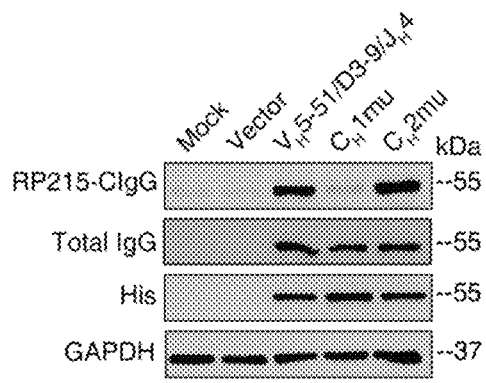

FIG. 1-2B

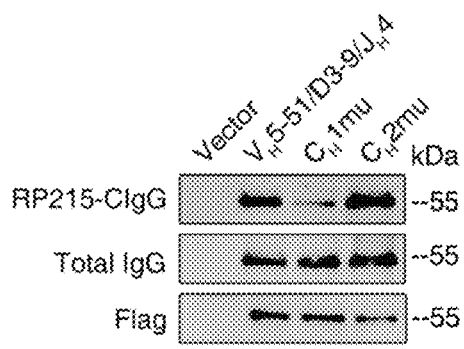

FIG. 1-2C

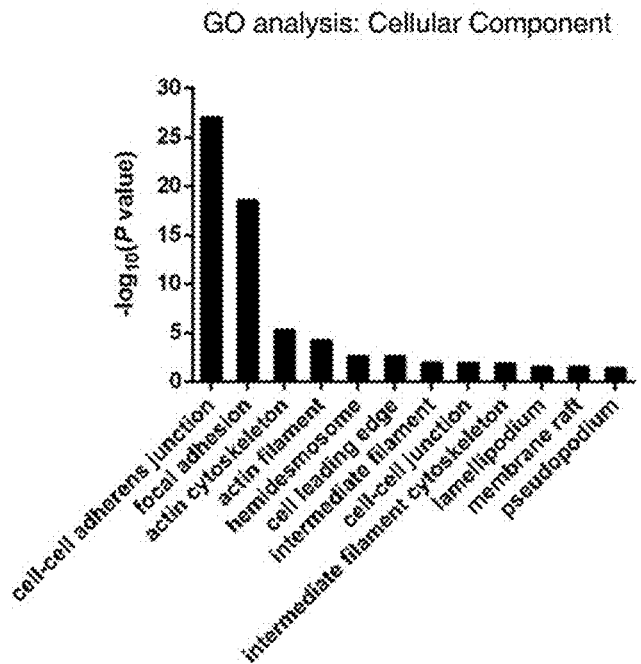

FIG. 4-1A

| Description | Sum PEP Score | Coverage | Peptides | PSMs | Unique Peptides |
|---|---|---|---|---|---|
| Isoform Beta-4A of Integrin beta-4 OS=Homo sapiens GN=ITGB4 | 446.479 | 49.37215 | 89 | 483 | 89 |
| Integrin alpha-6 OS=Homo sapiens GN=ITGA6 PE=1 SV=5 | 108.674 | 29.38053 | 31 | 98 | 31 |
| Isoform 3 of Integrin beta-1 OS=Homo sapiens GN=ITGB1 | 8.742 | 2.060606 | 13 | 15 | 13 |
| Isoform 2 of Integrin alpha-3 OS=Homo sapiens GN=ITGA3 | 9.285 | 3.377111 | 3 | 5 | 3 |
| CD44 antigen OS=Homo sapiens GN=CD44 PE=1 SV=3 | 3.416 | 1.617251 | 1 | 2 | 1 |
| Isoform 8 of Filamin-B OS=Homo sapiens GN=FLNB | 133.358 | 13.10292 | 28 | 64 | 24 |
| Hepatocyte growth factor receptor OS=Homo sapiens GN=MET PE=1 SV=4 | 98.357 | 19.28057 | 27 | 89 | 27 |
| Epidermal growth factor receptor OS=Homo sapiens GN=EGFR PE=1 SV=2 | 43.119 | 10.66116 | 13 | 35 | 13 |
| Actin-related protein 2/3 complex subunit 2 OS=Homo sapiens GN=ARPC2 PE=1 SV=1 | 47.748 | 37 | 11 | 37 | 11 |
| Ezrin OS=Homo sapiens GN=EZR PE=1 SV=4 | 19.944 | 9.5802 | 8 | 19 | 1 |
| Isoform 4 of Alpha-actinin-1 OS=Homo sapiens GN=ACTN1 | 63.792 | 17.52686 | 14 | 35 | 8 |

FIG. 4-1B

| Sample ID | RP215-IgG+ | RP215-IgG- | RP215-IgG+ ITGB4+ | RP215-IgG- ITGB4+ |
|---|---|---|---|---|
| 1 | 73.8% | 26.2% | 81.2% | 42.2% |
| 2 | 74.9% | 25.1% | 94.5% | 68.6% |
| 3 | 29.7% | 71.3% | 92.6% | 57.2% |
| 4 | 72.4% | 27.6% | 86.7% | 46.4% |
| 5 | 58.9% | 41.1% | 79.3% | 14.1% |

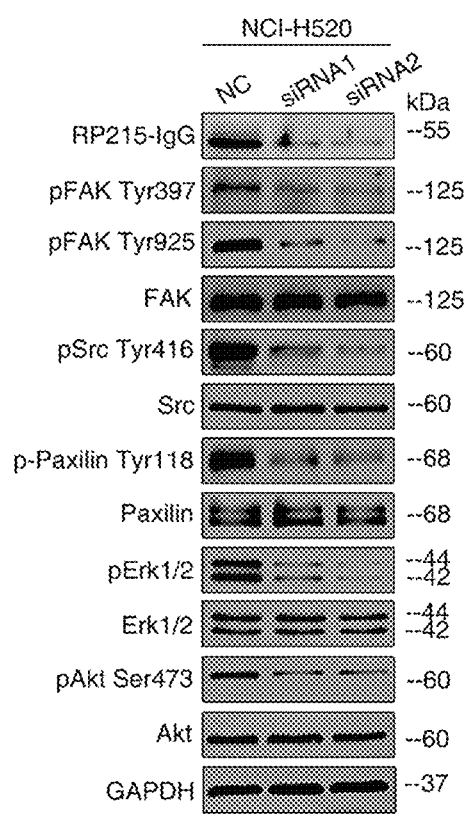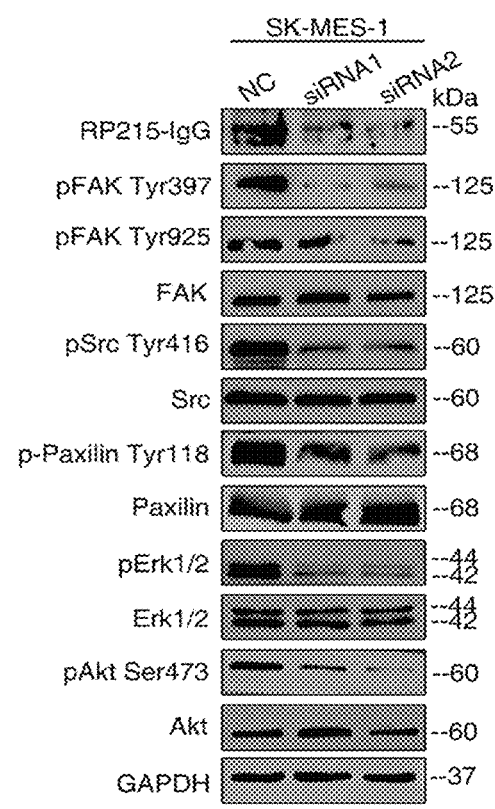
FIG. 4-6A  FIG. 4-6B

| Description | Sum PEP Score | Coverage | Peptides | PSMs | Unique Peptides |
|---|---|---|---|---|---|
| Isoform Beta-4A of Integrin beta-4 OS=Homo sapiens GN=ITGB4 | 446.479 | 49.37215 | 89 | 483 | 89 |
| Integrin alpha-6 OS=Homo sapiens GN=ITGA6 PE=1 SV=5 | 108.674 | 29.36053 | 31 | 96 | 31 |
| Isoform 3 of Integrin beta-1 OS=Homo sapiens GN=ITGB1 | 8.742 | 2.060606 | 13 | 15 | 13 |
| Isoform 2 of Integrin alpha-3 OS=Homo sapiens GN=ITGA3 | 9.265 | 3.377111 | 3 | 5 | 3 |
| CD44 antigen OS=Homo sapiens GN=CD44 PE=1 SV=3 | 3.416 | 1.617251 | 1 | 2 | 1 |
| Isoform 8 of Filamin-B OS=Homo sapiens GN=FLNB | 133.359 | 13.10292 | 28 | 64 | 24 |
| Hepatocyte growth factor receptor OS=Homo sapiens GN=MET PE=1 SV=4 | 98.357 | 19.28057 | 27 | 89 | 27 |
| Epidermal growth factor receptor OS=Homo sapiens GN=EGFR PE=1 SV=2 | 43.119 | 10.66116 | 13 | 35 | 13 |
| Actin-related protein 2/3 complex subunit 2 OS=Homo sapiens GN=ARPC2 PE=1 SV=1 | 47.748 | 37 | 11 | 37 | 11 |
| Ezrin OS=Homo sapiens GN=EZR PE=1 SV=4 | 19.944 | 9.5802 | 8 | 19 | 1 |
| Isoform 4 of Alpha-actinin-1 OS=Homo sapiens GN=ACTN1 | 63.792 | 17.52688 | 14 | 35 | 6 |

FIG. 4-7

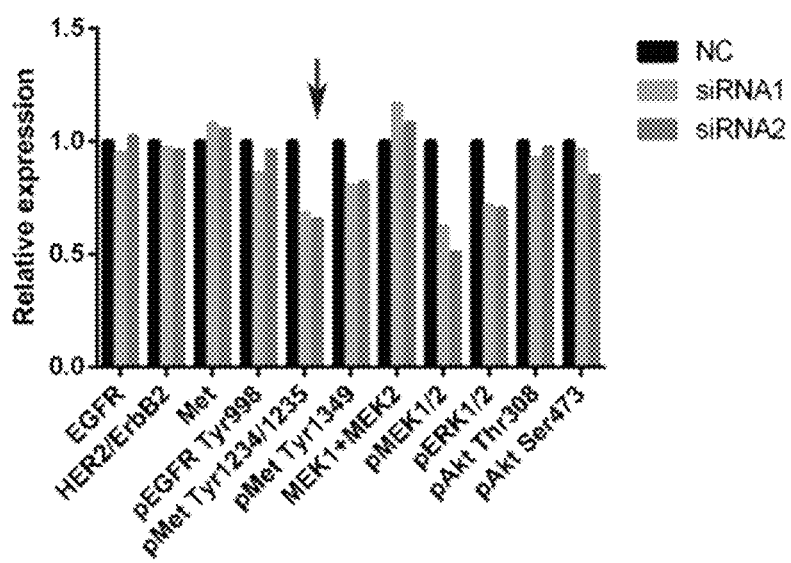

FIG. 4-8A

IgG EPITOPE AND APPLICATIONS THEREOF AS A DRUG TARGET

CROSS REFERENCE TO THE RELATED APPLICATIONS

This application is the national phase entry of International Application No. PCT/CN2018/099279, filed on Aug. 8, 2018, which is based upon and claims priority to Chinese Patent Application No. 201810146884.X, filed on Feb. 12, 2018 and Chinese Patent Application No. 201810330585.1, filed on Apr. 13, 2018.

SEQUENCE LISTING

The present application contains a Sequence Listing which has been submitted in ASCII format via EFS-Web and is hereby incorporated by reference in its entirety. Said ASCII copy is named GBBJTH001_ST25_20221206.txt, created 12/6/2022, and 5,111 bytes in size.

TECHNICAL FIELD

The present invention belongs to the general technical field of tumor diagnosis and treatment in immunology, and relates to a non-B cell-derived IgG, in particular to an IgG epitope and applications thereof as a drug target.

BACKGROUND

Source and existing research of RP215 monoclonal antibody: In 1980s, in order to obtain monoclonal antibodies specifically recognizing ovarian cancer, the Lee research group of Columbia University in Canada immunized animals with proteins extracted from ovarian cancer cell lines and acquired nearly 3,000 hybridoma cells. They found a hybridoma cell could recognize ovarian cancer cells but not normal ovarian cells, called RP215, but they did not which antigens it recognized at that time, so the antigen it recognized was temporarily named "CA215". Later it was found that, RP215 not only recognized ovarian cancer well, but also showed good specificity in recognizing other types of tumor cells, thus CA215 was defined as "pan-cancer-marker". In 2017, Lee research group identified CA215. They obtained a large amount of "CA215" from the culture supernatant of ovarian cancer cell lines using affinity chromatography. The 32 peptide fragments provided by mass spectrometry were all IgG heavy chains. In order to further confirm this result, they used the purified "CA215" as the antigen to prepare five strains of specific monoclonal antibodies. The experiments confirmed that all of the five monoclonal antibodies recognized IgG molecules. It proved that CA215 was IgG expressed by cancer cells. Subsequent results confirmed that the glycosylation of IgG expressed by cancer cells was significantly different from that of the circulating IgG. The epitope recognized by RP215 is the glycosyl-related epitope unique to this type of IgG heavy chain variable region (refer to Chinese Patent Publication No. 102901817A).

In other words, RP215 could not recognize IgG (circulating IgG) secreted by B lymphocytes after differentiation into plasma cells, but it could recognize IgG expressed by non-B cells. Studies have shown that the IgG recognized by RP215 (hereinafter referred to as RP215-IgG) can be expressed by cells of different lineages of cancers, but not or a few in normal non-B cells, so it is collectively referred to as non-B cell-derived IgG (non B-IgG). Non-B-IgG is greatly different from the traditional B cell-derived IgG in the structure and functions.

RP215-IgG that is overexpressed by tumor stem-like cells, tends to be located at the junction between the cell surface and the cell, especially the focal adhesion structure. In addition, high-level RP215-IgG cells have a high adhesion capacity to the extracellular matrix (ECM), high migration and invasiveness in vitro and in vivo, to enhance the self-renewal and tumor formation ability of tumor stem cells. However, the specific structure and nature of the unique epitope recognized by RP215 and the mechanism of RP215-IgG-driven tumor occurrence and development are still unknown, so it is impossible to prepare the drugs for diagnosis or treatment specifically targeting IgG other than RP215.

Through our efforts, we have been clearly aware that, IgG that can be specifically recognized by RP215 is non-B cell-derived IgG, and the recognized site on the IgG is highly sialylated, and the sialylated glycosyl group is not related with O-glycosylation. This special sialylated IgG can be used as a marker to identify stem cells or progenitor cells, and then prepare related preparations based on the glycoprotein.

In view of the close correlation between non-B cell-derived IgG and epithelial cancer cells, further studies on the molecular structure of the IgG will facilitate the intervention of various malignant tumors.

SUMMARY

The object of the present invention is to identify an epitope that can be used as a target through the further studies on the molecular structures and functions of non-B cell-derived IgG and provide new uses of the epitope.

Non-B cell-derived IgG was finally found through the related protease digestion analysis, glycosylation analysis and protein functional site analysis, and its tumor-related functions mainly depended on the sialylation of specific sites.

Based on our study results, the first aspect of the present invention provides an IgG epitope, which is the $C_H1$ domain of non-B cell-derived IgG, and has N-glycosylated sialic acid modification at Asn162 site of the domain.

Alternatively or preferably, the amino acid sequence of the foregoing IgG epitope is shown as SEQ ID NO: 1.

The second aspect of the present invention provides application of the IgG epitope in preparing drugs for diagnosis and/or treatment of tumors, and the tumors are epithelial tumors. The IgG containing the sialylated epitope at Asn162 specific site has been shown to promote tumor proliferation, migration and invasion ability.

Alternatively or preferably, in the above application, the tumors are non-small cell lung cancer, intestinal cancer, breast cancer, prostate cancer, kidney cancer, bladder cancer, saliva gland cystadenocarcinoma, gastric cancer, pancreatic cancer or esophageal cancer.

The third aspect of the present invention provides the application of the IgG epitope as a ligand of integrin α6β4 in preparing drugs for diagnosis and/or treatment of diseases mediated by α6β4-FAK-c-Met pathway. Studies have shown that IgG containing the epitope and integrin α6β4 bind to form a complex to promote the activation of integrin-FAK signaling pathway.

The fourth aspect of the present invention provides the application of sialyltransferase ST3GAL4 as a drug target in preparing tumor therapeutic drugs, and the tumors are epithelial tumors. The sialylation of the specific site containing the epitope depends on sialyltransferase ST3GAL4.

The present invention further provides the application of sialyltransferase ST3GAL4 combined with sialyltransferase ST3GAL6 as a drug target in preparing tumor therapeutic drugs, and the tumors are epithelial tumors. Studies have shown that sialyltransferase ST3GAL6 has an auxiliary role in the sialylation process of the epitope-specific site, therefore, the combination of them can be used as a drug target to intervene the epitope sialylation, thereby affecting its subsequent functions.

The fourth aspect of the present invention further provides the application of integrin β4 as a marker in preparing drugs for auxiliary detection of epithelial tumors. IgG containing the epitope and integrin β4 are co-expressed and co-localized at the tissue level and the cellular level, therefore, when integrin β4 is detected, equivalently, IgG is detected and epithelial tumors are detected.

According to the above technical solutions provided herein, the present invention has the following beneficial effects:

The present invention has identified the functional molecular structure of non-B cell-derived IgG, which is a highly sialylated structure of N-glycan at the Asn162 site on the $C_H1$ domain of IgG. It is over-expressed in stem cells of epithelial tumors and is very important to the carcinogenic properties of a variety of epithelial malignancies; in addition, it is an attractive target for antibody therapy, Car-T cell therapy and small molecule compounds, which provides an effective drug target for the treatment of related cancers and an epitope for antibody drug research.

BRIEF DESCRIPTION OF THE DRAWINGS

FIG. 1-1B: Structural diagram of each carbohydrate chain and the content of different glycans in Embodiment 1;

FIG. 1-1C: SNA and MAL I that recognized sialic acid were used to identify the status of IgG sialic acid in each component of affinity chromatography column in Embodiment 1;

FIG. 1-1D: Western blot results of sialylated IgG after digested with N-glycosidase, O-glycosidase and sialidase, respectively. Elution: eluent; buffer1: digestion buffer of N-glycosidase and O-glycosidase; buffer2: digestion buffer of sialidase in Embodiment 1.

FIG. 1-2A: Amino acid sequences of unmutated RP215-IgG (WT) (SEQ ID NO: 1) and two mutant ($C_H1$mu) (SEQ ID NO: 2) and ($C_H2$mu) (SEQ ID NO: 3), the framed part is the corresponding mutation site in Embodiment 1;

FIG. 1-2B: Detection of the recognition of RP215 by Western blot after over-expressing RP215-IgG (the variable region sequence is VH5-51/D3-9/JH4) and the corresponding mutant in 293T cells in Embodiment 1;

FIG. 1-2C: Detection of the recognition of RP215 by Western blot after overexpressing RP215-IgG (the variable region sequence is VH5-51/D3-9/JH4) and the corresponding mutant in NCI-H520 cells; where, mock is a negative control and vector is an empty vector in Embodiment 1.

FIG. 2-1A: Western blots to detect the expression of RP215-IgG in non-small cell lung cancer cell lines, GAPDH is the internal reference in Embodiment 2;

FIG. 2-1B: Western blots to detect the secretion of RP215-IgG in the culture supernatant of NCI-H520 cells and SK-MES-1 cells in Embodiment 2;

FIG. 2-1C: Immunofluorescence method to detect the localization of RP215-IgG in NCI-H520 cells and SK-MES-1 cells, Hochest labeled nuclei, secondary antibody: goat anti-mouse Alexa Flour 488, Scale 25 μm in Embodiment 2;

FIG. 2-1D: Flow cytometry to detect the expression of RP215-IgG on the cell membrane of non-small cell lung cancer cell line (live cell staining), secondary antibody: goat anti-mouse Alexa Flour 488 in Embodiment 2.

FIG. 2-2A: Western blot detection of knockdown after NCI-H520 cells are transfected with control or siRNA against IgG, respectively. GAPDH is internal reference in Embodiment 2;

FIG. 2-2B: NCI-H520 cells are transfected with siRNA for 36 h, then Transwell assay is performed to detect cell migration ability in Embodiment 2;

FIG. 2-2C: NCI-H520 cells are transfected with siRNA for 36 h, then Matrigel-Transwell assay is performed to detect the cell invasion ability in Embodiment 2;

FIG. 2-2D: Western blot detect the result of knockdown after knockdown of IgG in SK-MES-1 with IgG siRNA, GAPDH is internal reference;

FIG. 2-2E: SK-MES-1 cells are transfected with siRNA for 36 h, then Transwell assay was conducted to detect the cell migration ability in Embodiment 2;

FIG. 2-2F: SK-MES-1 cells are transfected with siRNA for 36 h, and then Matrigel-Transwell assay was conducted to detect the invasive ability. *, $P<0.05$; **, $P<0.01$; scale 200 μm.

FIG. 2-3A: Colony formation assay was performed to detect cell proliferation and self-renewal after knockdown of IgG for NCI-H520 cells in Embodiment 2;

FIG. 2-3B: Colony formation assay was performed to detect cell proliferation and self-renewal after knockdown of IgG for SK-MES-1 cells in Embodiment 2. **, $P<0.01$.

FIG. 2-4A: Western blot to detect RP215 recognition, commercial anti-human IgG is a negative control, GAPDH is an internal reference in Embodiment 2;

FIG. 2-4 B: Plate clonality assay results in Embodiment 2;

FIG. 2-4 C: Transwell assay to detect the cell migration ability in Embodiment 2;

FIG. 2-4D: Matrigel-Transwell assay to detect cell invasion ability. WT: Wild type IgG, $C_H1$mu: $C_H1$ mutant IgG; Vector: control empty vector; mock: negative control. ns, not significant; *, $P<0.05$; , $P<0.01$; *, $P<0.001$ in Embodiment 2.

FIG. 2-5A: Pictures of tumor volumes in WT, $C_H1$mu and Vector groups at the end of the experiment in Embodiment 2;

FIG. 2-5B: Growth curve of tumor volumes in WT, $C_H1$mu and Vector groups in Embodiment 2;

FIG. 2-5C: Tumor volumes graph in WT, $C_H1$mu and Vector groups at the end of the experiment in Embodiment 2;

FIG. 2-5D: Tumor weights graph in WT, $C_H1$mu and Vector group at the end of the experiment in Embodiment 2. ns, not significant; , $P<0.01$; *, $P<0.001$.

FIG. 3-1A: The result of RP215 recognition after silence of four sialyltransferases in Embodiment 3;

FIG. 3-1B: The result of RP215 recognition after over-expression of four sialyltransferases, of which, GAPDH is an internal reference in Embodiment 3.

FIG. 3-2 shows the immunohistochemical detection results of RP215, anti-ST3GAL4 and anti-ST3GAL6 antibodies in lung adenocarcinoma and lung squamous cell carcinoma tissues in Embodiment 3.

FIG. 4-1A: Gene Ontology analysis results of RP215-IgG specific interacting protein in Embodiment 4;

FIG. 4-1B: GO term analysis method to analyze proteins with high score of MS peptide segments in Embodiment 4.

FIG. 4-2A: Western blot results of integrin β1, integrin β4, integrin α6 antibody and RP215 after RP215 and NCI-H520 cell lysate are incubated for immunoprecipitation in Embodiment 4;

FIG. 4-2B: Western blot results of integrin β4 antibody and RP215 after integrin β4 antibody and NCI-H520 cell lysate are incubated for immunoprecipitation in Embodiment 4;

FIG. 4-2C: Western blot results of integrin α6 antibody and RP215 after integrin α6 antibody and NCI-H520 cell lysate are incubated for immunoprecipitation. mIgG is a control antibody, rIgG is a rabbit antibody, as a co-IP control in Embodiment 4.

FIG. 4-3 shows the immunohistochemical detection of staining and localization of RP215-IgG and integrin β4 in lung squamous cell carcinoma tissues, and the adjacent squamous cell carcinoma tissue sections showed similar staining patterns of RP215 and integrin β4 antibody in Embodiment 4. Scale, 50 μm.

FIG. 4-4A: Flow cytometry to analyze the expression levels of RP215-IgG and integrin β4 on the cell surface of lung squamous cell carcinoma PDX models in Embodiment 4. The analysis strategy: firstly, cell debris is excluded by cell size and particle size gate, live cells are obtained by 7-AAD negative cell gate, then the RP215-IgG positive and RP215-IgG negative cell populations are obtained by RP215-FITC gate; and then the integrin β4 expression levels of the above two cell populations are analyzed by anti-integrin β4-PE;

FIG. 4-4B: Flow cytometry to sort out NCI-H520 cells with strong positive and weak positive RP215, and Western blots to detect the expression level of integrin β4 in the cells with high expression of RP215-IgG (RP215-IgG$^{high}$) and low expression of RP215-IgG (RP215-IgG$^{low}$) in Embodiment 4.

FIG. 4-5 shows the immunofluorescence analysis of the location of RP215-CIgG (first column from the left) and integrin β4 (second column from the left) in NCI-H520 cells in Embodiment 4. Scale, 10 μm.

FIG. 4-6A: NCI-H520 cells are transfected with control or siRNA against IgG, respectively in Embodiment 4. Western blots are used to detect knockdown effects and molecules related to the Integrin-FAK signaling pathway. GAPDH is an internal reference.

FIG. 4-6B: SK-MES-1 cells are transfected with control or siRNA against IgG, respectively in Embodiment 4. Western blots are used to detect knockdown effects and molecules related to the Integrin-FAK signaling pathway. GAPDH is internal reference.

FIG. 4-7 shows partial mass spectrometry scoring result of RP215-IgG specific interacting proteins in Embodiment 4.

FIG. 4-8A: Statistical results of straining after NCI-H520 cells are transfected with control or siRNA against IgG, respectively, and incubated in cell lysate and RTK phosphorylation chips in Embodiment 4;

FIG. 4-8B: Statistical results of straining after SK-MES-1 cells are transfected with control or siRNA against IgG, respectively, and incubated in cell lysate and RTK phosphorylation chips in Embodiment 4.

FIG. 4-9A: NCI-H520 cells are transfected with control or siRNA against IgG, respectively. Western blots are used to detect knockdown effect and c-Met phosphorylation level and related molecules of downstream signaling pathway. GAPDH is an internal reference in Embodiment 4.

FIG. 4-9B: SK-MES-1 cells are transfected with control or siRNA against IgG, respectively. Western blots are used to detect the knockdown effect and c-Met phosphorylation level and related molecules of downstream signaling pathways in Embodiment 4. GAPDH is an internal reference.

FIG. 4-10A: RP215 and c-Met antibody are incubated with NCI-H520 cell lysate for immunoprecipitation, and Western blots detection is performed with c-Met antibody and RP215 in Embodiment 4;

FIG. 4-10B: NCI-H520 cells are transfected with control siRNA and c-Met siRNA, respectively, and Western blots are used to detect the knockdown effect in Embodiment 4. RP215 is incubated with NCI-H520 cell lysate transfected with control siRNA and c-Met siRNA, respectively, and Western blots detection is performed with integrin β4 antibody and RP215;

FIG. 4-10C: The knockdown effect detected by Western blots after NCI-H520 cells are transfected with control siRNA and integrin β4 siRNA in Embodiment 4. Antibody RP215 is incubated with NCI-H520 cell lysate transfected with control siRNA and integrin β4 siRNA, respectively, and Western blots detection is performed with c-Met antibody and RP215.

FIG. 4-11A: The experimental results on the inhibition of Integrin-FAK signaling pathway of NCI-H520 cells after exogenous addition of antibody RP215 in Embodiment 4. Add control antibody mIgG (50 μg/ml) or different concentrations of antibody RP215 (2 μg/ml, 10 μg/ml, 50 μg/ml) in the cell culture supernatant of NCI-H520. Cells are collected at 12 h, 24 h and 36 h, and Integrin-FAK signaling pathway is detected by Western blots;

FIG. 4-11B: The experimental results on the inhibition of clone formation ability of NCI-H520 cells after exogenous addition of antibody RP215 in Embodiment 4. Add control antibody mIgG (50 μg/ml) or different concentrations of antibody RP215 (2 μg/ml, 10 μg/ml, 50 μg/ml) in the cell culture supernatant of NCI-H520. Colony formation ability is detected by colony forming assay. ns, not significant; P<0.001.

FIG. 4-12A: The experimental results on the inhibition of Integrin-FAK signaling pathway of SK-MES-1 cells after exogenous addition of RP215-IgG reversible antibody RP215 in Embodiment 4. SK-MES-1 cell culture supernatant is added with antibody RP215 (10 μg/ml) and different concentrations of RP215-CIgG (2 μg/ml, 10 ng/ml, 50 μg/ml) or flow-through liquid components (10 μg/ml, 50 μg/ml). The cells are collected at 48 h, and Western blot is performed to detect the Integrin-FAK signaling pathway.

FIG. 4-12B. The experimental results on the inhibition of colony formation ability of SK-MES-1 cells after exogenous addition of RP215-IgG reversible antibody RP215 in Embodiment 4. SK-MES-1 cell culture supernatant is added with antibody RP215 (10 ng/ml) and different concentrations of RP215-CIgG (2 μg/ml, 10 ng/ml, 50 μg/ml) or flow-through liquid components (10 μg/ml, 50 μg/ml). The culture results and statistical results of colony formation ability detected by colony formation assay. ns, not significant: ***, P<0.001.

FIG. 5A: Immunohistochemical staining score results in 242 lung cancer tissues in Embodiment 5;

FIG. 5B: Immunohistochemical staining sections of RP215-IgG in tissues of patients with different types of lung cancer in Embodiment 5;

FIG. 5C: RP215 immunohistochemical staining results of normal alveolar tissues (Alveolus), drainage lymph node tissues (Lymph node) and bronchial tissues (Bronchus) in Embodiment 5;

FIG. 5D: Kaplan-Meier survival curve analysis of the correlation between RP215 staining score grade and 5-7 year survival rate of patients with lung squamous cell carcinoma in Embodiment 5.

FIG. 6A: Schematic diagram of the experimental procedure of antitumor in vivo experiment using RP215 in Embodiment 7;

FIG. 6B: Tumor changes after injecting RP215 (monoclonal antibody) and control mIgG, respectively in Embodiment 7;

DETAILED DESCRIPTION OF THE EMBODIMENTS

In the following embodiments, RP215-IgG refers to IgG that can be specifically recognized by monoclonal antibody RP215, and it is non-B cell-derived IgG.

Sources of Biological Materials:

Monoclonal Antibody RP215:

For hybridoma cell line, RP215-containing ascites was produced by culturing hybridoma clones in the abdominal cavity of BALB/c mice sensitized with Freund's adjuvant. According to the manufacturer's description, antibodies were purified from ascites using protein G affinity chromatography (GE healthcare, USA), then concentrated and obtained using PBS as a solvent.

Cancer Cell Lines:

The LSCC cell lines NCI-H520, SK-MES-1 and 293T were obtained from American Type Culture Collection (ATCC, Manassas, VA, USA) and kept by the Center for Human Genomics, Peking University.

Example 1 Functional Structure Determination of RP215-IgG

1. Purification of IgG from Cancer Tissues (1) Tumor IgG was purified from the PDX tumor models established by non-small cell lung cancer tissues, breast cancer or ovarian cancer tissues, or lung squamous cell carcinoma (LSCC) tissues in advance using protein G-Sepharose 4 Fast Flow (GE healthcare, USA). The use of PDX tumor models was to exclude the effect of IgG derived from peripheral blood.

(2) Purification of RP215-IgG with RP215 affinity column.

Figures 1, 1A:
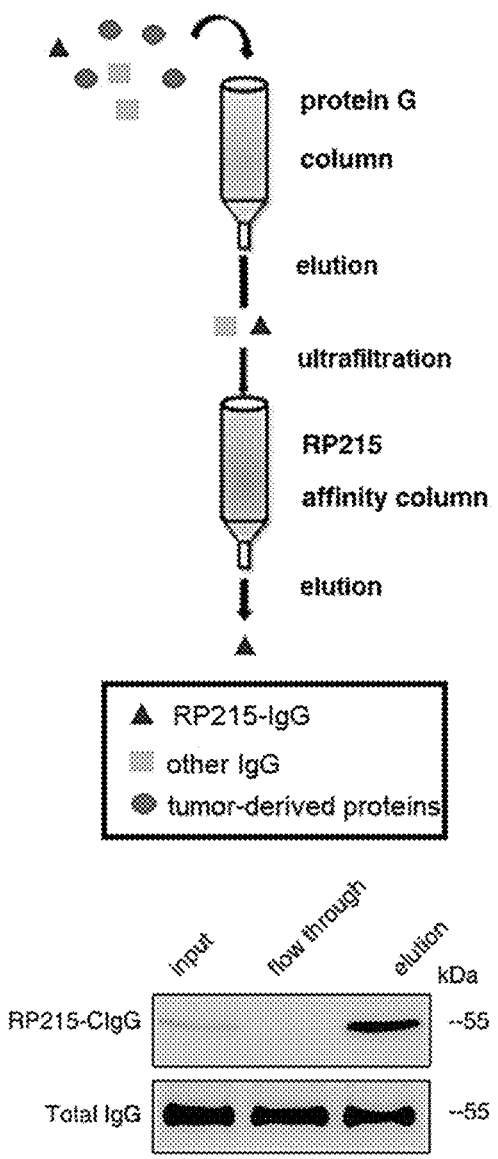
FIG. 1-1A: Schematic diagram of IgG recognized by RP215 enriched from lung squamous cell carcinoma using ProteinG combined with RP215-CNBr affinity chromatography column in Embodiment 1.

Preparation of RP215 affinity column: the monoclonal antibody RP215 was coupled with Sepharose 4 Fast Flow (GE Healthcare, USA) activated by CNBr, as shown in FIG. 1-1A. The operations were performed according to the instructions. ① After 330 mg CNBr-sepharese 4B was activated with 1 mM hydrochloric acid, it was equilibrated with coupling buffer (0.1M NaHCO$_3$, 0.5M NaCl, pH8.3). ② 5 mg of RP215 antibody was dissolved in coupling buffer, then added into the activated CNBr agarose gel filler and incubated overnight at 4° ° C. ③ At 4° C., the coupled gel was washed with Tris-HCl (pH 8.0, 0.1 M) and resuspended overnight to block the unconjugated activation site. ④ The affinity column was washed alternately with acidic washing solution (0.1M NaAc, 0.5M NaCl, pH 4.0) and alkaline washing solution (0.1M Tris, 0.5M NaCl, pH 8.0) at least 3 times to remove excessive RP215.

Purification of RP215-IgG with RP215 affinity columns: about 5 mg of tumor IgG that was adjusted to 1 μg/μl in PBS was incubated with the affinity column at 4° C. overnight to bind RP215 on the affinity column to tumor IgG. ⑥ After washing with at least 5 column volumes of PBS, elution procedure was performed using 0.1 M Tris-glycine (pH 2.4). The eluate was collected and concentrated with PBS ultrafiltration for further analysis. The concentrated eluate contained the separated IgG, which was labeled RP215-IgG.

2. IgG Glycosylation Analysis

Release of N-Glycan

50 μg of RP215-IgG, 2.5 μL of 200 mM DTT and 150 μL of 20 mM ammonium bicarbonate buffer were added to an ultrafiltration reactor (PALL, USA), incubated at 50° C. for 1 hour, then added with 10 ul of 200 mM IAA to the solution. The mixture was incubated at room temperature for 45 minutes in the darkness to denature the protein. The denatured protein was washed twice with 200 ul of 20 mM ammonium bicarbonate buffer. 1 μl of PNGase F and 200 ul of 20 mM ammonium bicarbonate buffer were added to the reactor. Then the mixture was further incubated at 37° C. overnight to achieve complex release of N-glycan.

After centrifugation, the released solution containing N-glycan was collected. Prior to derivatization, the solution was lyophilized.

UPLC-HRMS Analysis of N-Glycan:

Prior to UPLC-HRMS analysis, the collected N-glycan was added to the derivatization solution. The derivatization solution included 10 μl aqueous solution containing 1 μl 10% acetic acid, 7 μl of isopropanol containing 30 mg/ml of 2,4-bis(diethylamino)-6-hydrazino-1,3,5-triazine and 2 μl of water. The derivatization reaction was completed at 37° C. for 2 hours.

The derivatized products were further analyzed directly by UPLC-Orbitrap (Thermo Fisher Scientific, Bremen, Germany) without any further purification. The mobile phase A was a 10 mM ammonium formate aqueous solution. The mobile phase B was acetonitrile. The mobile phase A increased from 20% to 50% within 15 minutes, holding for 5 minutes. Then mobile phase A decreased to 20% within 5 minutes, holding for 5 minutes. The flow rate was 0.4 ml/min, the column temperature was 10° C., and the injection volume was 3 μl. The ESI voltage was set to 3.2 kV for quality data collection, and 35 arb sheath gases and 10 arb auxiliary gases were applied to stabilize the ESI. Derivatized oligosaccharides were detected in a positive mode. The full scan quality range was from 800 to 3000 m/z.

Figures 1, 1B:
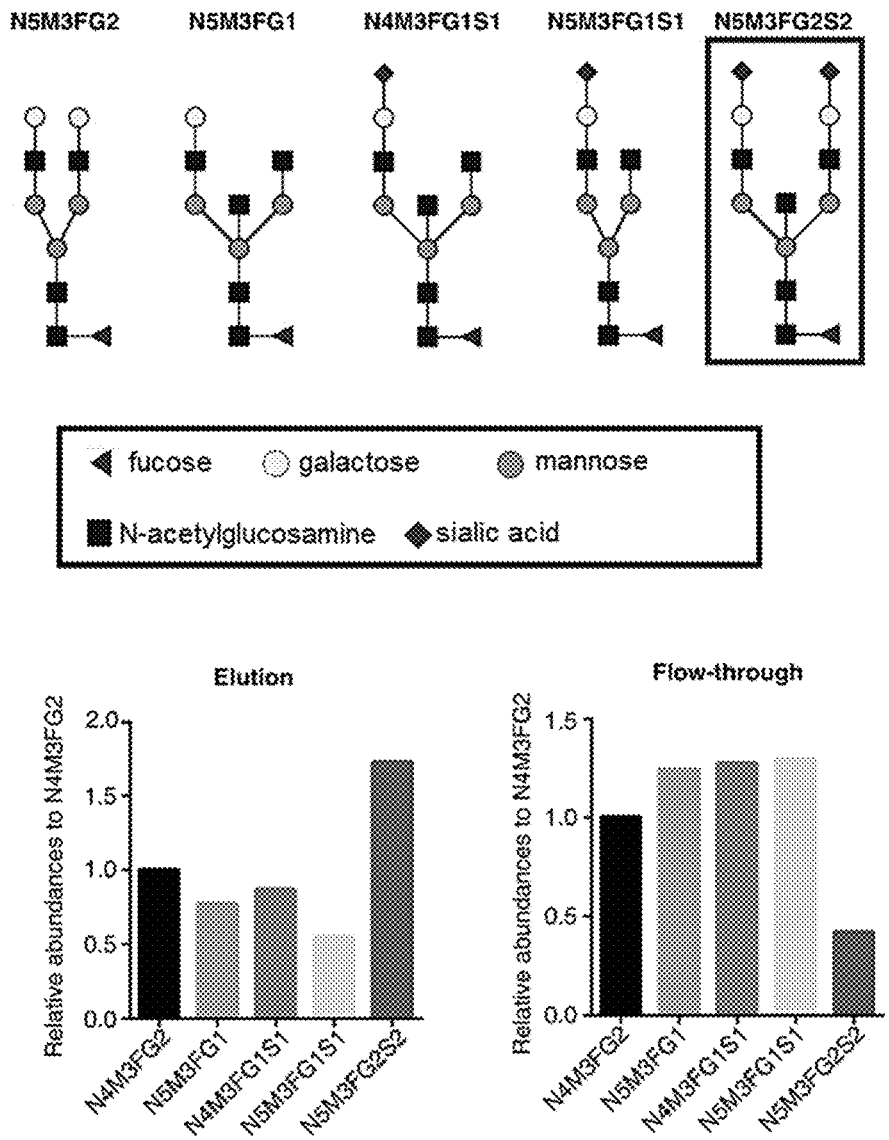

The results showed that 28 types of N-glycan were detected, including fucose and sialic acid that were not commonly found in circulating IgG. Four types of glycans: N5M3FG2 and N5M3FG1 (both without sialic acid), and N4M3FG1S1 and N5M3FG1S1 (both containing a terminal sialic acid residue) had a higher unbound component in RP215, while the ratio of N5M3FG2S2 (with a sialylation biantennary structure) in the unbound components of RP215 was significantly reduced (FIG. 1-1B). In contrast, N5M3FG2S2 had a higher abundance in the RP215 binding components (FIG. 1-1B).

3. Analysis of IgG Epitope Sites

Glycosylation Analysis of Recognition Sites:

The purified RP215-IgG was deglycosylated.

The eluent in the above section 1 (containing RP215-IgG, labeled as elution) was taken as the sample. In order to digest N-linked and O-linked glycans, the sample was added to the denaturation buffer and denatured at 100° C. for 10 minutes. Then, the above mixture was incubated in G7 reaction buffer containing NP-40 and an appropriate amount of glycosidase for 2 hours at 37° C. to digest the protein.

Glycosidase was N-glycosidase (PNGase F) (NEB, USA). PNGase F could hydrolyze almost all N-carbohydrate chain; O-glycosidase (NEB, USA) could hydrolyze O-carbohydrate chain;

In order to digest sialic acid, the samples were digested in G1 reaction buffer containing nueraminidase (Sialidase) (NEB, USA) for 2 hours at 37° C.

Figures 1, 1C:
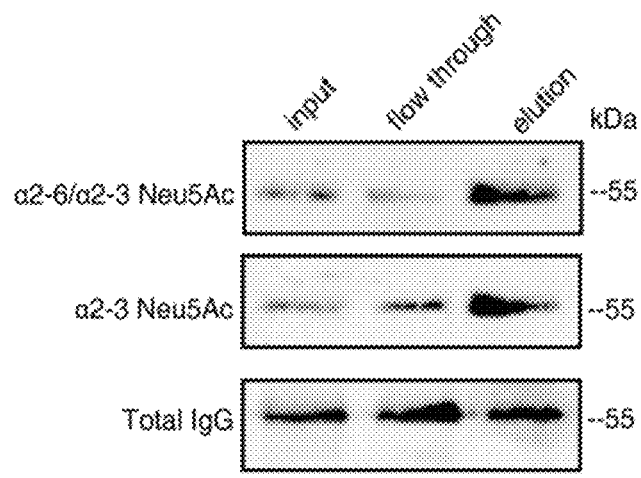
Figures 1, 1D:
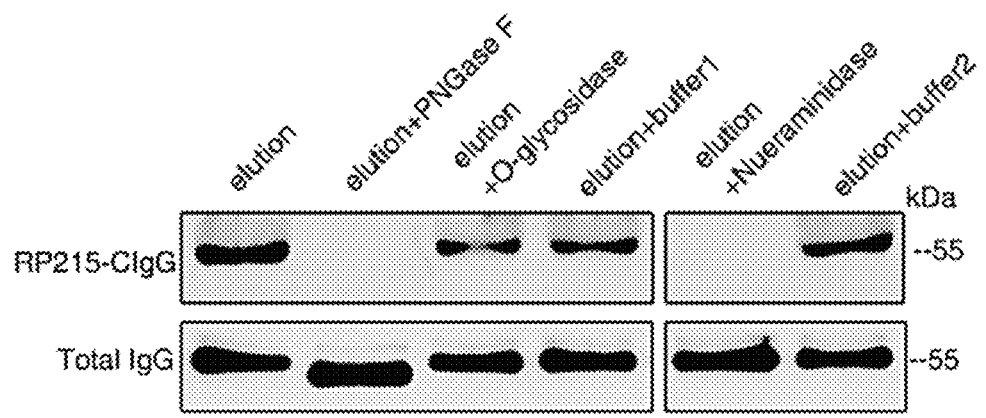

The experimental results were shown in FIG. 1-1D. After treatment with PNGaseF and neuraminidase, the band recognized by RP215 disappeared, and RP215 recognition was not disturbed after digestion with O-glycosidase. In addition, we found that the molecular weight of all N-linked carbohydrates between the innermost GlcNAc and Asn residues of RP215-IgG decreased from 55 kD to 50 kD, while IgG treated with O-glycosidase remained unchanged. The above results indicated that the epitope recognized by RP215 was related to the sialic acid residue of N-glycan on IgG.

FIG. 1-1A electropherogram showed that the purified elution product (containing the target IgG) could be recognized by RP215, and the input band of sample solution that did not pass through column was slightly displayed, while the flow-through liquid could not be recognized by RP215.

FIG. 1-1C showed the test results of identifying whether the RP215 affinity column could enrich sialylation IgG using lectins that could specifically recognize sialic acid—Sambucusnigra agglutinin (SNA) that mainly recognized sialic acid linked by α2,6, Maackiaamurensis leukoagglutinin I (MAL I) that mainly recognized sialic acid linked by α2,3. Results showed that the eluent contained sialic acid linked by α 2, 6 and α 2,3.

4. Analysis of Sialylation Recognition Sites of RP215-IgG

The Fab fragment of IgG is composed of $C_H1$ and the variable region. The variable region shows a great diversity. We assume that the possible N-glycan sites recognized by RP215 may be located in $C_H1$. According to our previous studies, RP215 can recognize IgG from different tissues of epithelial cancer that has different VDJ recombination patterns, so it is speculated that the epitope recognized by RP215 is not on the variable region, but should be on $C_H1$. Therefore, the atypical glycosylation motifs TVSWN162SGAL (SEQ ID NO: 4) (S160A and N162C) found in the $C_H1$ domain were introduced with site-specific mutations for preliminary exploration. At the same time, the classic glycosylation site asparagine (N) 297 in the $C_H2$ domain was also introduced, which was replaced with glutamine (Q) as a control.

Figures 1A, 2:
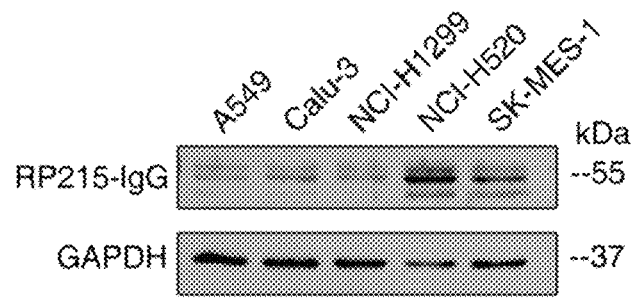
Figures 1B, 2:
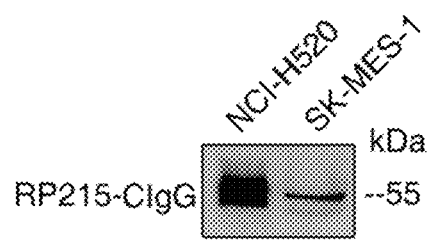
Figures 1C, 2:
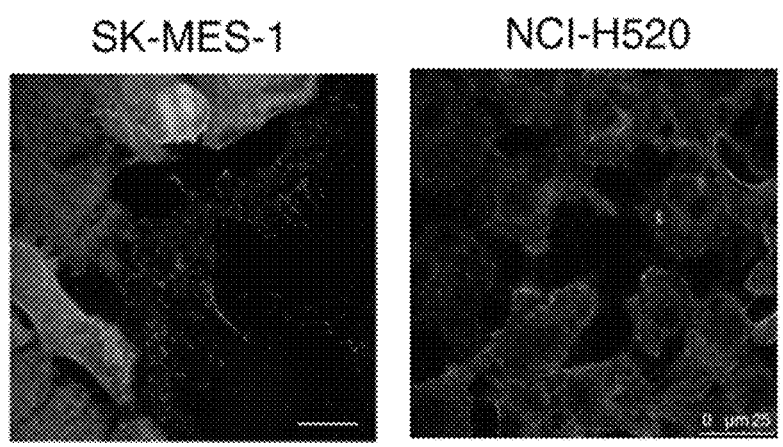
Figures 1D, 2:
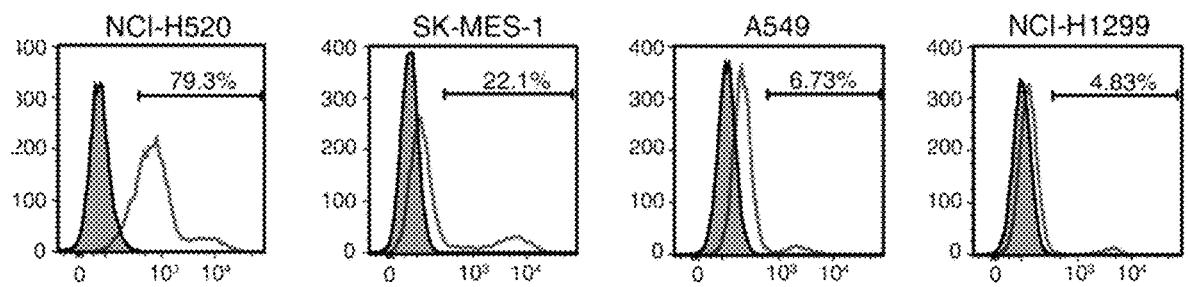
Figures 2, 2A:
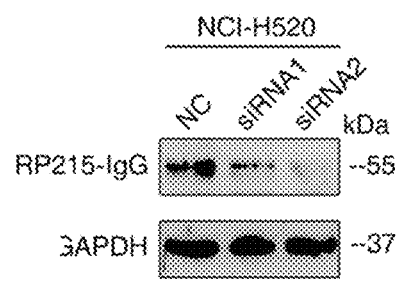

The mutation sites were shown in FIG. 1-2A, of which, WT represented wild type; $C_H1$mu represented mutation of site 162: S160A and N162C; $C_H2$mu represented mutation of site 297: N 297 Q.

Figures 2, 2B:
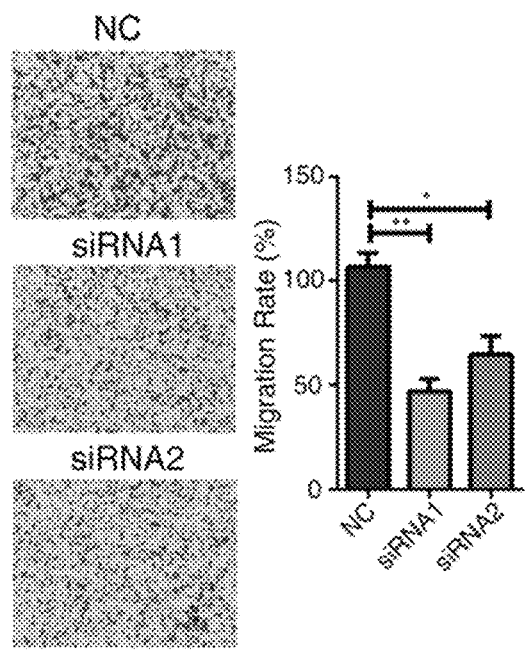

Two constant regions with mutation sites were fused with variable regions VH5-51/D3-9/JH4 (predominant expression sequences detected in lung squamous carcinoma cells), named $C_H1$mu and $C_H2$mu, respectively, at the same time, the wild type IgG (WT) with $C_H1$ and $C_H2$ domains was constructed as a control. Firstly, these recombinant IgG plasmids (WT, $C_H1$mu and $C_H2$mu) were over-expressed in 293T cells. Western blot was used to detect the recognition of wild-type and mutant IgG by RP215. Results showed that RP215 could recognize WT and $C_H2$mu, but could not recognize $C_H1$mu (FIG. 1-2B).

Figures 2, 2C:
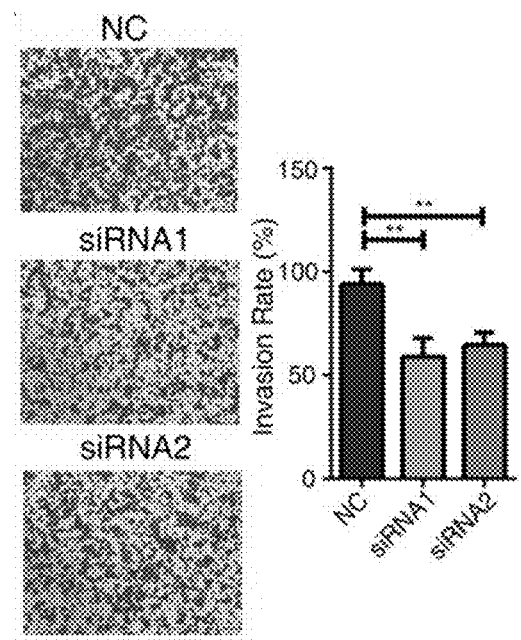
Figures 2, 2D:
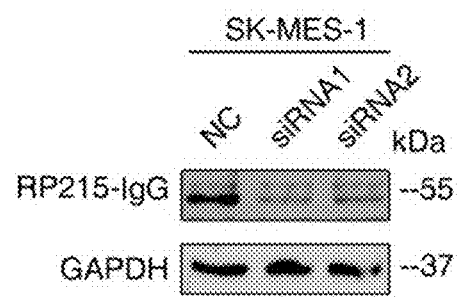
Figures 2, 2E:
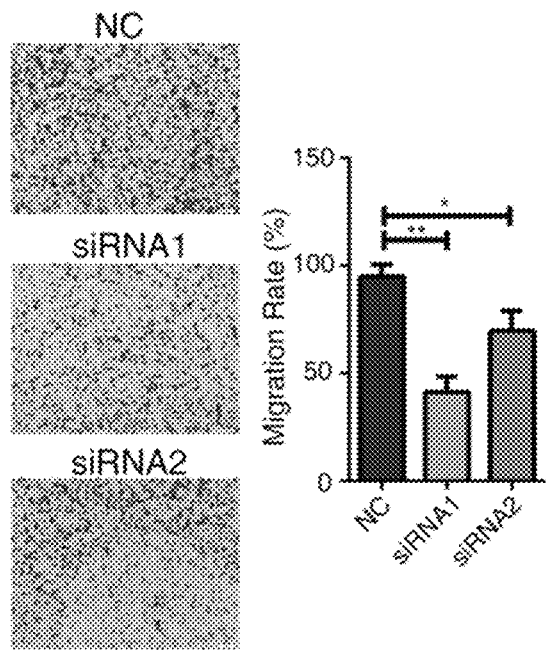
Figures 2, 2F:
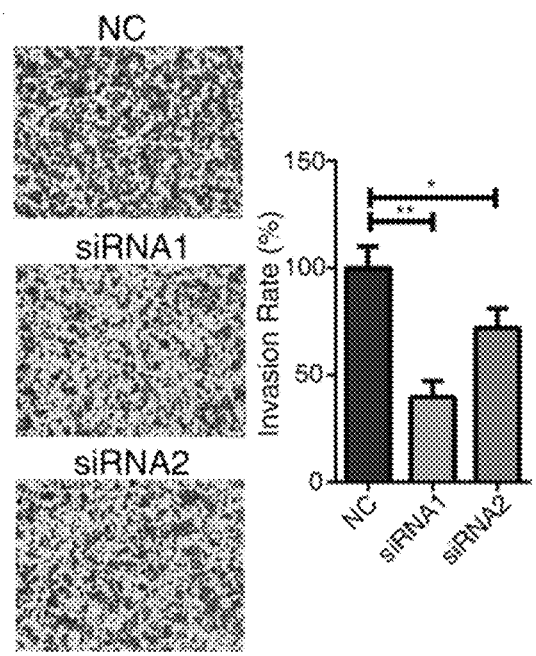

Next, we verified the epitope recognized by RP215 in the lung squamous carcinoma cell line NCI-H520, thereby eliminating the interference of endogenous RP215-IgG. We constructed a recombinant IgG plasmid with a flag tag, and then used anti-flag beads for IP to obtain exogenously expressing wild-type or mutant IgG. Similar to 293T results, RP215 could recognize WT or $C_H2$mu in NCI-H520 cells very well, but it could slightly recognize $C_H1$mu (see FIG. 1-2C).

The epitope recognized by RP215 on RP215-IgG was located in the non-classical N-glycosylation site Asn162 of the $C_H1$ domain, not the classic N-glycosylation site Asn297.

Therefore, the $C_H1$ domain with N-glycosylated sialic acid modification at Asn162 site could be used as a unique epitope for non-B cell-derived IgG.

Example 2 Identification of Non-B Cell-Derived IgG that has the Ability to Promote the Proliferation, Migration and Invasion of Tumor Cells Using IgG Epitope as a Target Example 1 confirmed the unique epitope of non-B cell-derived IgG, which could be specifically recognized by RP215, so using this epitope as a specific recognition site, RP215 was used to detect the functions of non-B cell-derived IgG (RP215-IgG).

NSCLC cell lines: A549 (human alveolar basal epithelial cells of adenocarcinoma), Calu-3 (human lung adenocarcinoma), NCI-H1299 (human lung adenocarcinoma), NCI-H520 (human lung squamous carcinoma cells), SK-MES-1 (human lung squamous carcinoma cells).

Firstly, we detected expression of RP215-IgG in the above several NSCLC cell lines, and found that RP215-IgG that could be expressed and secreted by NSCLC cell line was localized on the cell surface and ECM (shown in FIG. 2-1A-D).

When siRNAs targeting the heavy chain constant region in NCI-H520 cells and SK-MES-1 cells downregulated IgG, the size of clones formed by these cells was reduced, and the number of clones formed was also significantly reduced. In addition, in the Transwell and Matrigel-coated Transwell assays, the migration and invasion ability of cells was significantly reduced (FIG. 2-2A-F, FIG. 2-3A-B). In addition, similar experiments indicated that sialylated IgG was associated with cell migration, invasion and metastasis in lung ADC, breast cancer and kidney cancer.

In vitro experiments, the over-expression of wild-type IgG (WT) could apparently promote cell migration, invasion, and clone forming ability. After mutating the glycosylation site of $C_H1$ domain, compared with WT, $C_H1$ mutant IgG had a significantly reduced ability to promote cell migration, invasion and colony formation, and its activity had migration-promoting effect compared to the empty vector group, but there was no significant difference in invasion ability between them (FIG. 2-4A-D).

Further, we established subcutaneous tumorigenic models of NCI-H520 cells stably expressing wild-type IgG, $C_H1$ mutant IgG and empty vector in nude mice, to observe the tumor growth promoting ability of the wild-type IgG and $C_H1$ mutant IgG. Results showed that the over-expression of wild-type IgG could significantly promote the growth of tumors, while the cells grew slowly in the $C_H1$mu group, and its number, volume and weight of tumors formed were all significantly lower than those in the WT group, but were not significantly different from those in the empty vector group (FIG. 2-5A).

In summary, the in vivo and in vitro experiments have showed that RP215-IgG can promote the survival, migration and invasion of lung squamous cell carcinoma, and its biological activity depends on the non-classical glycosylation site of $C_H1$ domain.

Example 3 Sialyltransferase ST3GAL4 Involved in Sialylation of RP215-IgG

The biosynthesis of sialylation oligosaccharide sequences is catalyzed by a family of enzymes called sialyltransferase, and each sialyltransferase has its specific substrate.

Previous studies showed that the sialic acid linked to the N-glycan at the classical N-glycosylation site (Asn297) was mediated by sialytransferase ST6GAL-1, and the sialic acid was connected with N-glycan β-D-galactopyranosyl (Gal) residue by α 2,6-.

We have determined that the sialic acid linked to the N-glycan at the non-classical N-glycosylation site (Asn162) was connected to the β-D-galactopyranosyl (Gal) residue via MALI, therefore, the three sialyltransferases (ST3GAL3, ST3GAL4, ST3GAL6, involved in ST3β-galactoside α-2, 3-linkage) and ST6GAL1 (as a control) were the candidates for further screening.

In order to determine which sialyltransferase was involved in synthesis of RP215-IgG, RP215 was used in the Western blot of four sialyltransferase silencing. Results showed that, both ST3GAL4 and ST3GAL6 knockdown reduced the expression of RP215-IgG, and the over-expression of ST3GAL4 and ST3GAL6 resulted in an increase in the IgG recognized by RP215. It should be noted that, there was no change in Western blot of the commercial anti-IgG antibody, indicating that the IgG recognized by RP215 was greatly affected by sialic acid (Example 3-1).

In order to identify the relationship between sialylated IgG (i.e. RP215-IgG) and ST3GAL4/ST3GAL6, we analyzed the expression profile and distribution in NSCLC. Immunohistochemical results showed RP215-IgG and ST3GAL4 staining in bronchial epithelial basal cells in lung adenocarcinoma tissues and lung squamous cell carcinoma tissues, while the positive staining of ST3GAL6 was not restricted. IHC results showed that ST3GAL4 was more related to the sialylation of RP215-IgG (Example 3-2).

Therefore, blocking the activity of the ST3GAL4 enzyme can prevent the sialylation of IgG and thereby inhibit its function in tumor cell migration and invasion, and prevent the growth, migration and invasion of tumor cells.

Example 4 RP215-IgG Interacted with Integrin α6β4 and Cross-Linked with c-Met In order to explore the mechanism by which RP215-IgG promotes the proliferation, migration and invasion of lung squamous cell carcinoma, we first searched the RP215-IgG interacting protein. The lung squamous carcinoma cell line NCI-H520 protein was extracted, and RP215 was used for immunoprecipitation (immunoprecipitation, IP), then all proteins obtained by the antibody RP215 and the control antibody mIgG IP were analyzed by LC-MS/MS.

Figures 2, 3, 3A:
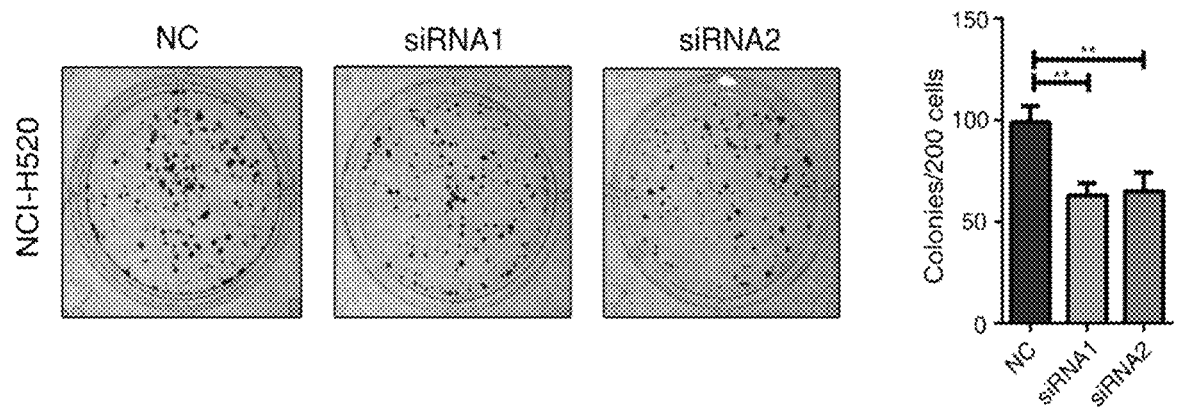
Figures 2, 3, 3B:
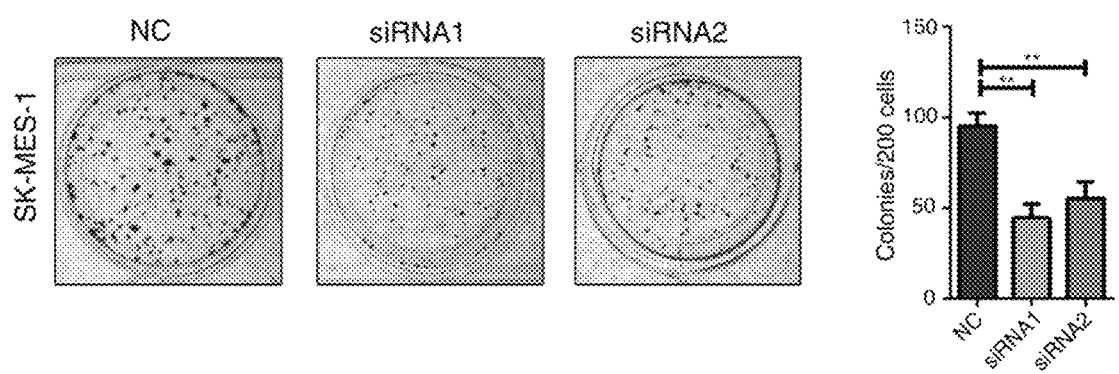
Figures 2, 3, 4, 4A:
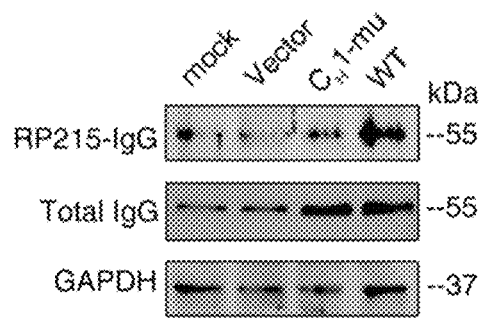

While the potentially interacting proteins were analyzed by MS, we quantified the relative abundance of these proteins by label-free quantification (LFQ) method. The protein obtained with RP215 IP was compared with the protein obtained with the negative control antibody mIgG IP, and we concluded that only the proteins with an LFQ value of zero in the mIgG group were proteins that could specifically interact with RP215-CIgG. Next, Gene Ontology (GO) analysis was conducted for all proteins screened from database david.ncifcrf.gov, that is, Gene Ontology Cellular Component analysis. Results showed that the protein components that specifically interacted with RP215-IgG were mainly cell membrane-related proteins, which were involved in the cell-cell adhesion junctions, focal adhesions, and formation of hemi-desmosomes (FIG. 4-1A). We further analyzed the protein components in these GO terms and compared their MS scores (results were shown in FIG. 4-1B), finally we chose to focus on integrin family, which played an important role in promoting tumorigenesis and metastasis based on several reports in the recent years.

In order to confirm our MS findings, we performed IP (immunoprecipitation) with RP215 and found that sialylated IgG (i.e. RP215-IgG) interacted with integrin β4 or integrin α6, but had no interaction with integrin β1. At the same time, immunoprecipitation was performed with integer β4 or integer α6, and RP215-IgG was detected in their affinity elution fractions, indicating the specific interaction between sialylated IgG and integrin α6β4 complex (FIG. 4-2A-C).

In order to clarify whether the expression of sialylated IgG is related to the expression of integrin β4, we first used clinical lung squamous cell carcinoma tissues to detect the tissue distribution pattern of sialylated IgG and integrin β4 on adjacent paraffin sections by immunohistochemistry. We found that both RP215 and anti-integrin β4 antibody had strong positive staining on the cell membrane in lung squamous cell carcinoma, and their distribution patterns were very similar (FIG. 4-3).

In addition, we explored the correlation between RP215-IgG and integrin β4 expression levels at the cellular level. We digested the tumor tissue of the lung squamous cell carcinoma PDX model with collagenase IV and DNase I to obtain a single cell suspension, and then analyzed their expressions on the cell membrane by flow cytometry. After viable cells were obtained with 7-AAD negative gates, RP215-IgG was highly expressed in PDX tumors. The further flow cytometry showed that the positive rate of integrin β4 in RP215-IgG positive cell population (79.3%-92.6%) was significantly higher than the positive rate of integrin β4 in RP215-IgG negative cell population (14.1%-57.2%) (FIG. 4-4A).

Figures 2, 3, 4, 4B:
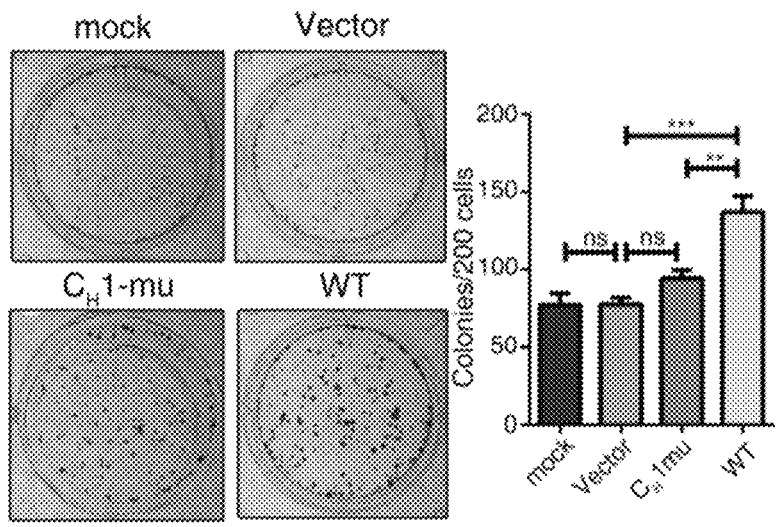
Figures 2, 3, 4, 4C:
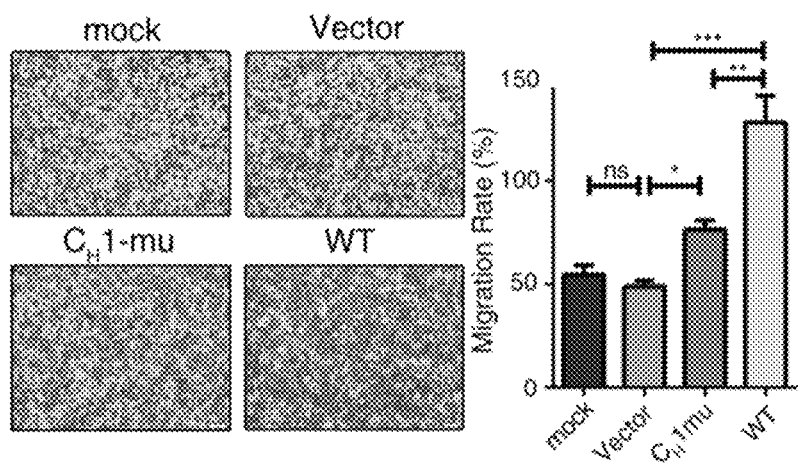
Figures 2, 3, 4, 4D:
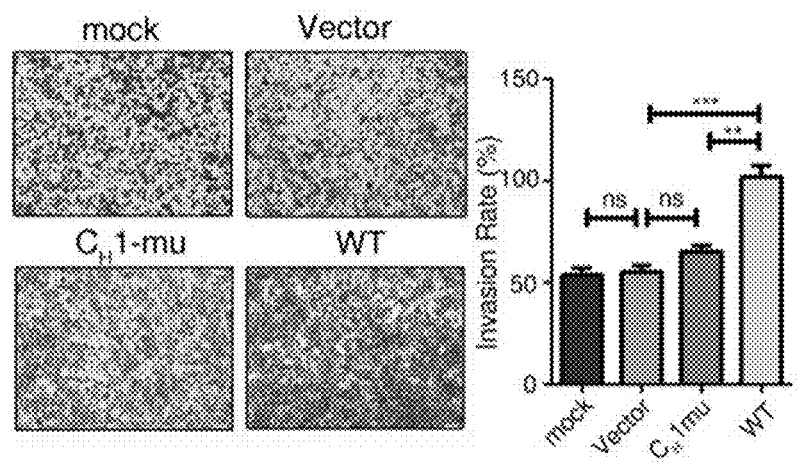

In addition, we evaluated the expression of integrin β4 in RP215-IgG positive cells in lung squamous carcinoma cell lines. We used flow cytometry sorting to obtain two groups of cells with high expression of sialylated IgG (RP215-IgGhigh) and low expression of sialylated IgG (RP215-IgGlow) by enrichment from NCI-H520 cell line, then the expression levels of integrin β4 in the two groups of cells were detected by Western blots. Results showed that RP215-IgG was positively correlated with integrin β4 protein expression level in LSCC cell line (FIG. 4-4B).

Figures 2, 3, 4, 5, 5A:
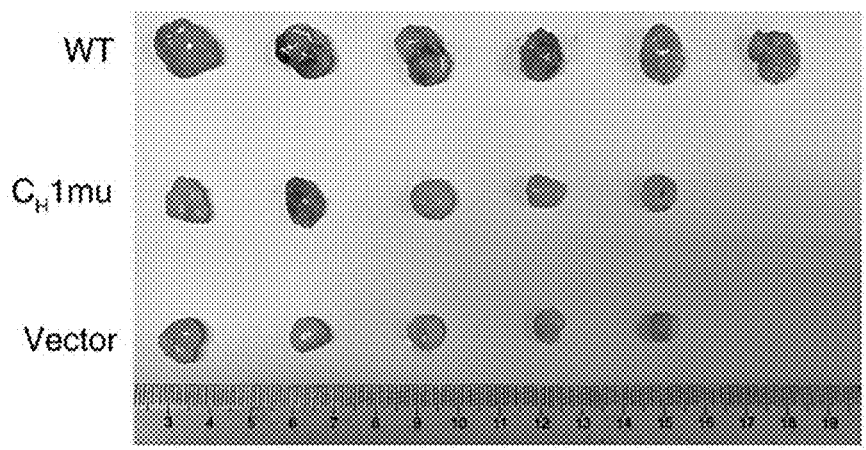

Finally, we detected the localization of RP215-IgG and integrin β4 in cells using immunofluorescence method. The results showed that, RP215-IgG was expressed in the cell membrane and cytoplasm, integrin β4 was mainly expressed on the cell membrane, and they had obvious co-localization on the cell membrane (FIG. 4-5).

In summary, we found that RP215-IgG and integrin β4 were co-expressed and co-localized at the tissue and cellular levels, which provided a basis for the interaction between them under natural conditions.

The co-expression and co-localization of RP215-IgG and integrin β4 also proved that integrin β4 could be used as a marker to characterize the distribution and expression of RP215-IgG, which could be used for the detection of RP215-IgG. Since RP215-IgG could promote the proliferation, migration and invasion of epithelial tumors, integrin β4 could be used as a marker for preparing drugs for the auxiliary detection of epithelial tumors.

In malignant tumor cells, integrin α6β4 has been shown to be associated with multiple receptor tyrosine kinases (RTK), which can amplify the signals to promote the invasion and metastasis of tumor cells. We used antibody RP215 to perform immunoprecipitation in NCI-H520 cells, and used mass spectrometry to find RP215-IgG interacting proteins. Results showed that c-Met and EGFR of the RTK family were also detected in the components bound to RP215, and their scores were relatively high, suggesting that interaction exists between RP215-IgG and the RTK family (FIG. 4-7).

In order to study the specific RTK activated by sialylated IgG, we knocked down IgG in NCI-H520 and SK-MES-1, and detected EGFR, HER2, c-Met in the RTK family and the level of phosphorylation of these key molecules related to RTK downstream signal transduction by phosphorylation chips. Results showed that, after knockdown of IgG in two cell lines, the phosphorylation level at the site Tyr1234/1235 of c-Met was significantly down-regulated, while the phosphorylation levels of EGFR and HER2 showed no significant change (FIG. 4-8A-B). At the same time, the phosphorylation levels of Ras-MAPK at the downstream of RTK and key molecules MEK, Erk1/2, and Akt of PI3K-Akt pathway were decreased significantly. We further confirmed the results of phosphorylation chips using Western blots (FIG. 4-9A-B).

Since IgG knockdown reduced Met tyrosine phosphorylation greatly, we explored how sialylated IgG formed complexes with integrin β4 or Met in LSCC.

First, we confirmed the interaction between RP215-IgG and c-Met in NCI-H520 cells by endogenous co-immunoprecipitation. Subsequently, we explored the interactions between RP215-IgG, integrin α6β4, and c-Met by co-immunoprecipitation method. We knocked down c-Met and integrin β4 in NCI-H520 cells respectively, and then used RP215 for immunoprecipitation. Results showed that, compared with the non-knockdown group NC, the knockdown of c-Met did not affect the interaction between RP215-IgG and integrin β4, but after knockdown of integrin β4, the interaction between RP215-IgG and c-Met disappeared (FIG. 4-10B, C). In conclusion, it suggested that sialylated IgG and integrin β4 must form a complex before interacting with Met.

The integrin-FAK and Met signaling pathways were involved in the cell proliferation and migration regulated by sialylated IgG.

Subsequently, we studied the molecular mechanism of sialylated IgG to promote the proliferation and migration of LSCC cell lines. The integrin family, as extracellular matrix protein receptor, has no intrinsic tyrosine kinase activity, but mainly performs signal transduction by recruiting and activating non-receptor tyrosine kinases. When binding to the corresponding ligand, integrin β4 can recruit focal adhesion kinase (FAK) through the domain of its cytoplasmic region, to phosphorylate the Tyr397 site of FAK, then bind to the SH2 domain of Src and promote the phosphorylation of Tyr416 site of Src; after phosphorylation of Src, the Tyr925 site of FAK can be phosphorylated through feedback regulation, which eventually leads to downstream Ras-MAPK or PI3K-Akt cascade reaction.

In order to identify whether sialylated IgG was involved in FAK or Met signaling, IgG was silenced in LSCC cell lines by siRNA. Apparently, after knocking down IgG with two different siRNAs, the phosphorylation levels of FAK and Src-related sites could be significantly down-regulated, indicating that the down-regulation of RP215-IgG expression level could lead to inactivation of FAK-Src signal transduction. In addition, as a member of the focal adhesion complex, paxilin is a direct activation target of FAK, and the up-regulation of phosphorylation level at the site Tyr118 can activate paxilin and function as a cytoskeletal adaptor protein, thereby activating cell movement or cell polarization-related signal paths. We also found that when IgG was knocked down, the phosphorylation level of paxilin at the site Tyr118 was also significantly inhibited (shown in FIG. 4-6A-B).

Because sialylated IgG could be secreted into the supernatant and co-localized with integrin β4 on the LSCC cell membrane, we used monoclonal antibody RP215 to block and destroy the complex formed by IgG and integrin β4, to investigate whether the observed changes in FAK signal in IgG-silenced LSCC cells were induced by secreted IgG. Compared with the isotype control, after treatment with RP215, the phosphorylation of FAK, Src, paxilin and Akt was significantly reduced in a concentration- and time-dependent manner, and the activation of Erk1/2 mediated by Met signal transduction was greatly reduced (experimental results were shown in FIG. 4-10A-C).

In order to further verify the effects of secretory IgG, exogenous sialylated IgG (RP215-IgG) purified from LSCC PDX tumors by RP215 affinity chromatography was added to the culture medium of NCI-H520 cells to rescue FAK signal transduction caused by exogenous addition of RP215 or knockdown of IgG. It was found that by incubating with RP215-IgG at an increased dose, the inhibition of FAK signal transduction was reversed gradually. In addition, exogenous addition of RP215-IgG could significantly rescue the decrease in clonal formation and migration ability caused by IgG knockdown, but the IgG components of flow-through liquid in RP215 affinity chromatography could not achieve this function (FIG. 4-11A-B and FIG. 4-12A-B).

In order to further study whether the activation of FAK signal transduction neutralized by sialylated IgG depended on its N-glycan modification of sialylation, RP215-IgG was digested with neuraminidase. When incubated with 10 μg/ml of RP215 for 36 hours, we did not observe the effect of RP215-IgG on FAK activity after digestion with neuraminidase, indicating that the functional activity of sialylated IgG depended on its sialic acid structure.

To sum up, integrin-FAK signal transduction is the key molecular mechanism of sialylated IgG to promote the proliferation and migration of cancer cells.

Previous studies have shown that sialylated IgG bound to integrin α6β4 to form a complex, to promote the activation of integrin-FAK signaling pathway. Therefore, sialylated IgG can be used as a ligand of integrin α6β4 for preparing drugs for the diagnosis or treatment of diseases mediated by α6β4-FAK pathway. Of course, the Asn162 site of $C_H1$ domain of the IgG is modified by N-glycosylated sialic acid.

Example 5 Specific Labeling of Non-Small Cell Lung Cancer with RP215-IgG

Patient Samples:

Formalin-fixed, paraffin-embedded lung cancer tissue sections were obtained from 242 patients in Harbin Medical University Cancer Hospital (Harbin, Heilongjiang Province). The clinicopathological features were available from the review of medical records. The diagnosis and histological classification of tumor specimens were based on WHO classification. The stage of tumor-lymph node metastasis (TNM) was determined according to the guidelines of the American Joint Committee on Cancer (AJCC).

All patients were 25 to 82 (56.6±10.6) years old, including 121 cases of SCC (squamous cell carcinoma), 76 cases of ADC (lung adenocarcinoma), 21 cases of SCLC (small cell lung cancer), 5 cases of large cell lung cancer, 5 cases of bronchoalveolar carcinoma, and 14 cases of undifferentiated carcinoma. 62 patients (25.6%) were women. In terms of histopathological grading, 26.8% of samples (65 cases) were well differentiated (grade I), 49.2% (119 cases) were moderately differentiated (grade II), and 24.0% (58 cases) were poorly differentiated (grade 3). According to the TNM staging criteria, 134 patients (55.4%) were in stage I, 50 patients (20.7%) were in stage II, 56 patients (23.1%) were in stage III, and 2 patients (0.8%) were in stage IV.

The sialylated IgG was determined using the monoclonal antibody RP215 in 242 cancer tissues of patients with different types of lung cancer.

We first found a high expression of sialylated IgG in NSCLC (140/221, 63%), but not found in SCLC (0/21). In addition, sialylated IgG was expressed at high frequency in SCC (102/121, 84.3%) in NSCLC cases; while expressed at low frequency in ADC (28/76, 36.8%), small cell lung cancer (2/5, 40.0%) and undifferentiated cancer (8/14, 57.1%); no staining was observed in bronchoalveolar carcinoma (0/5).

We compared the expression pattern and pathological score of sialylated IgG, and found that all cancer cells, especially the cell surface, showed very strong staining (score: 110.9) in sialylated IgG positive tissues of SCC. However, only a few cancer cells showed weak or moderate staining in non-SCC tissues (score: 21.1), indicating that the sialylated IgG could also promote the progression of NSCLC, and sialylated IgG on the cell surface of SCC could be used as a target for lung SCC therapy.

Figures 2, 3, 4, 5, 5B:
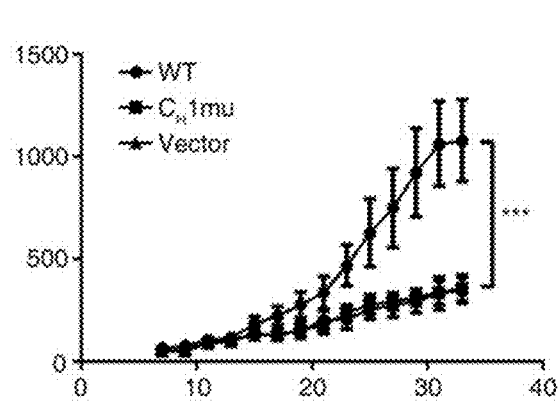
Figures 2, 3, 4, 5, 5C:
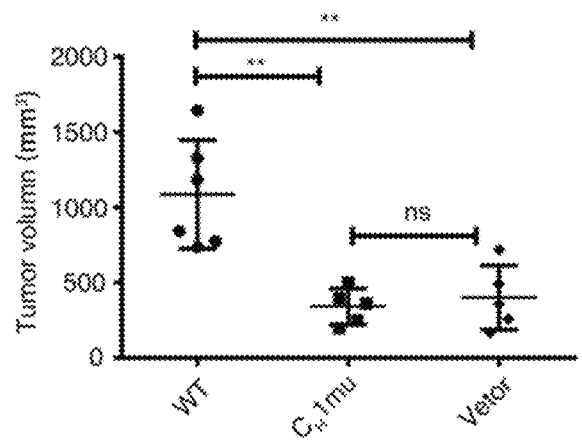
Figures 2, 3, 4, 5, 5D:
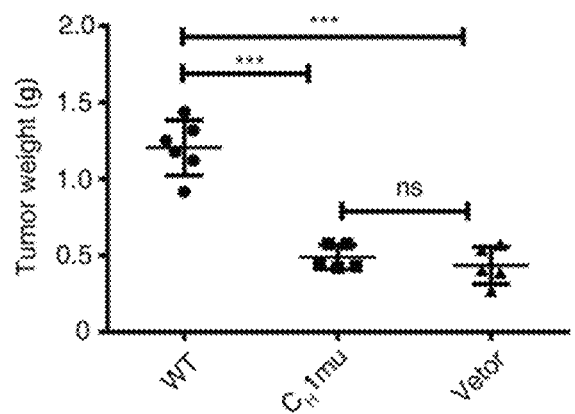
Figures 1A, 3:
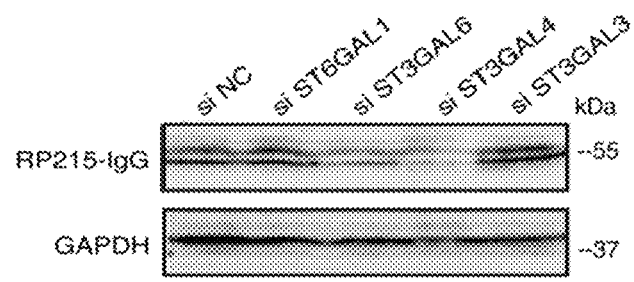
Figures 1B, 3:
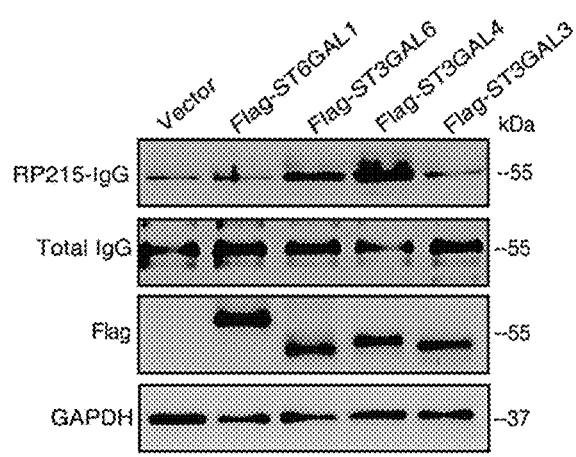
Figures 2, 3:
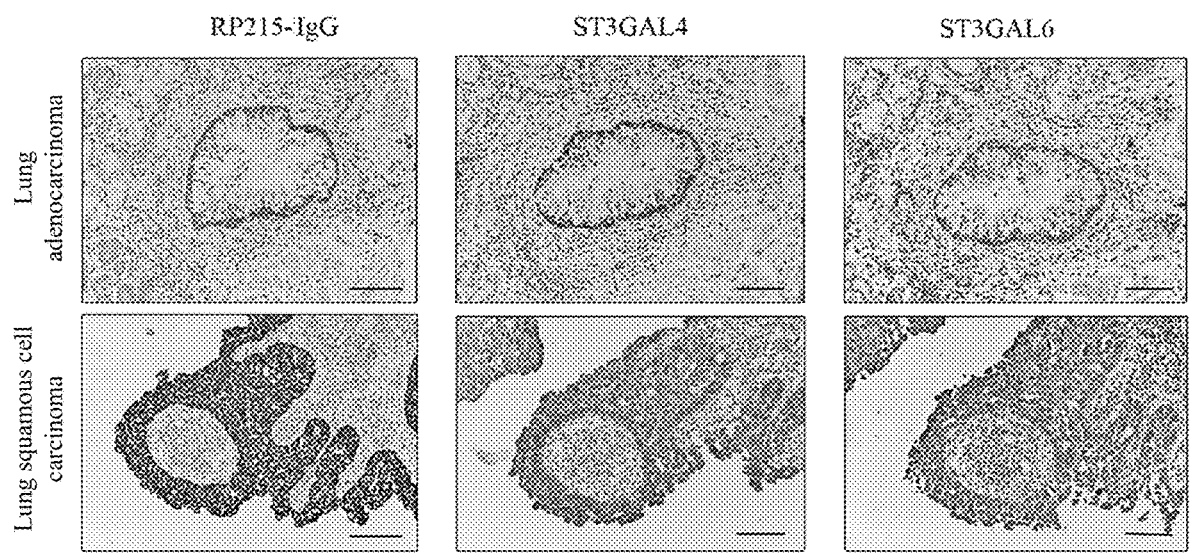
Figures 2A, 4:
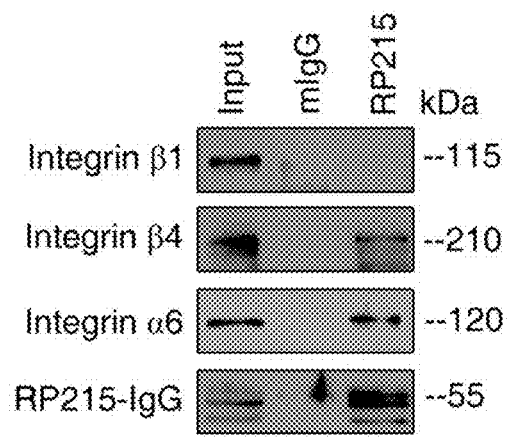
Figures 2B, 4:
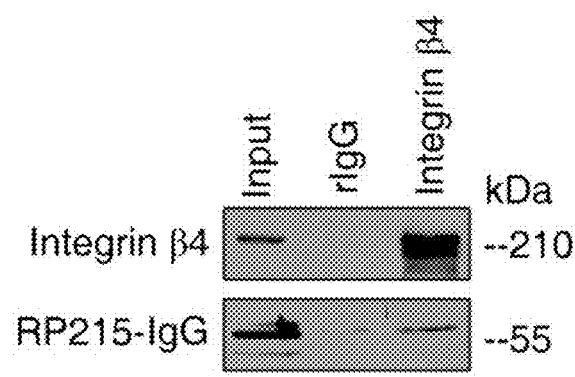
Figures 2C, 4:
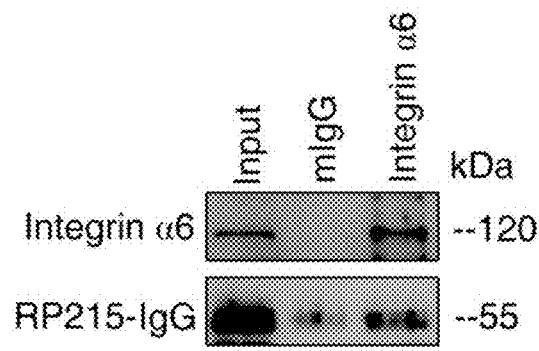
Figures 3, 4:
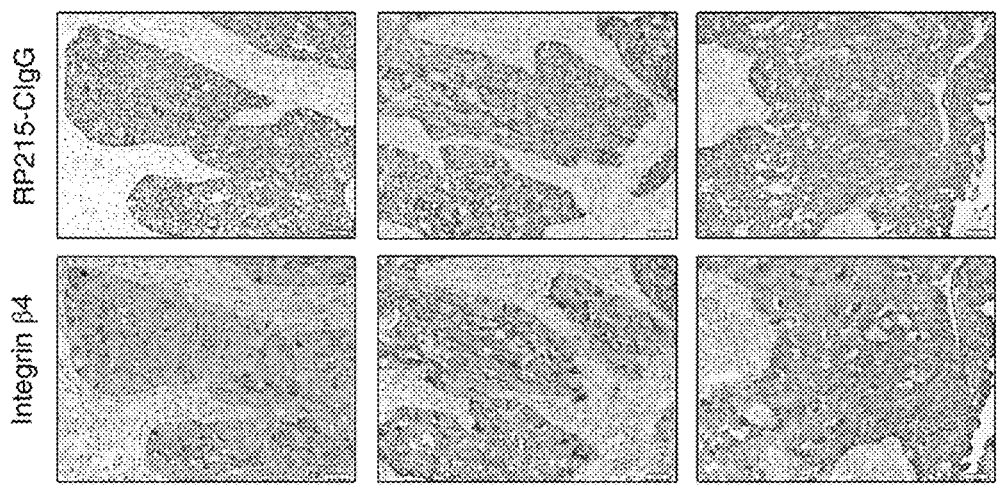
Figures 4, 4A:
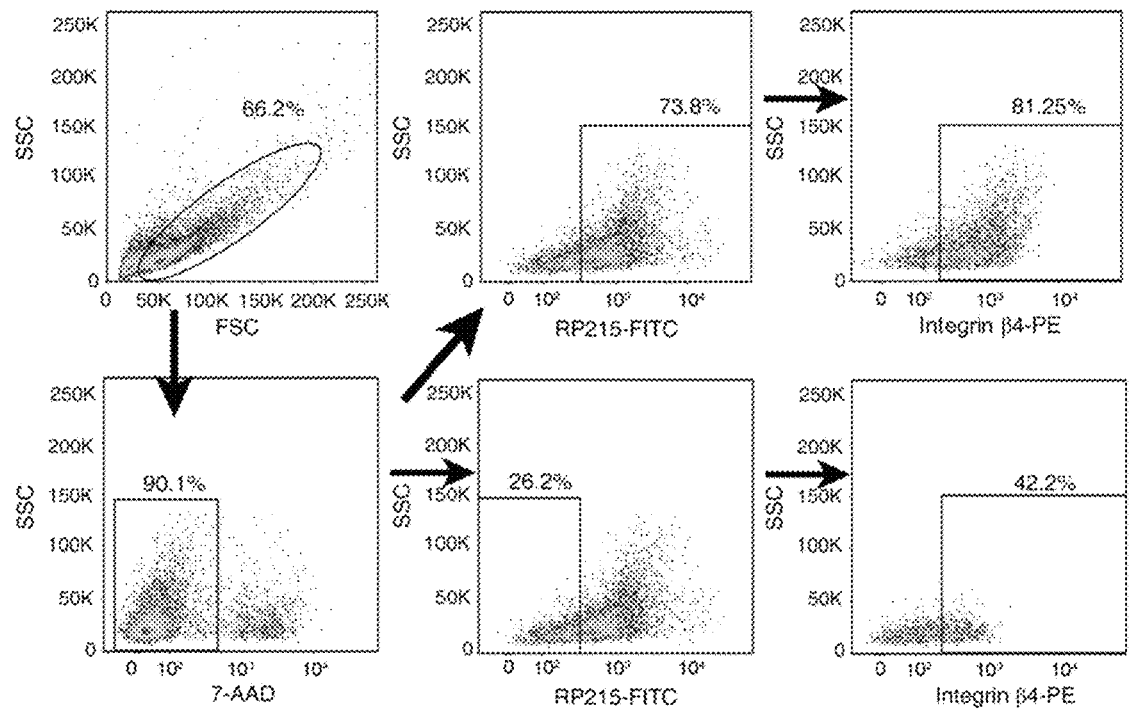
Figures 4, 4B:
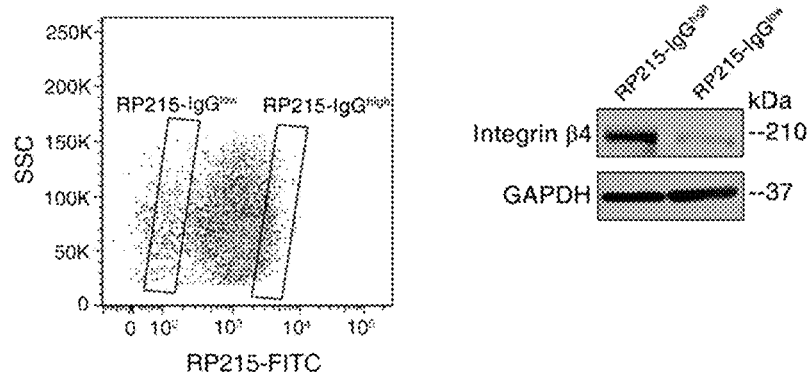
Figures 4, 5:
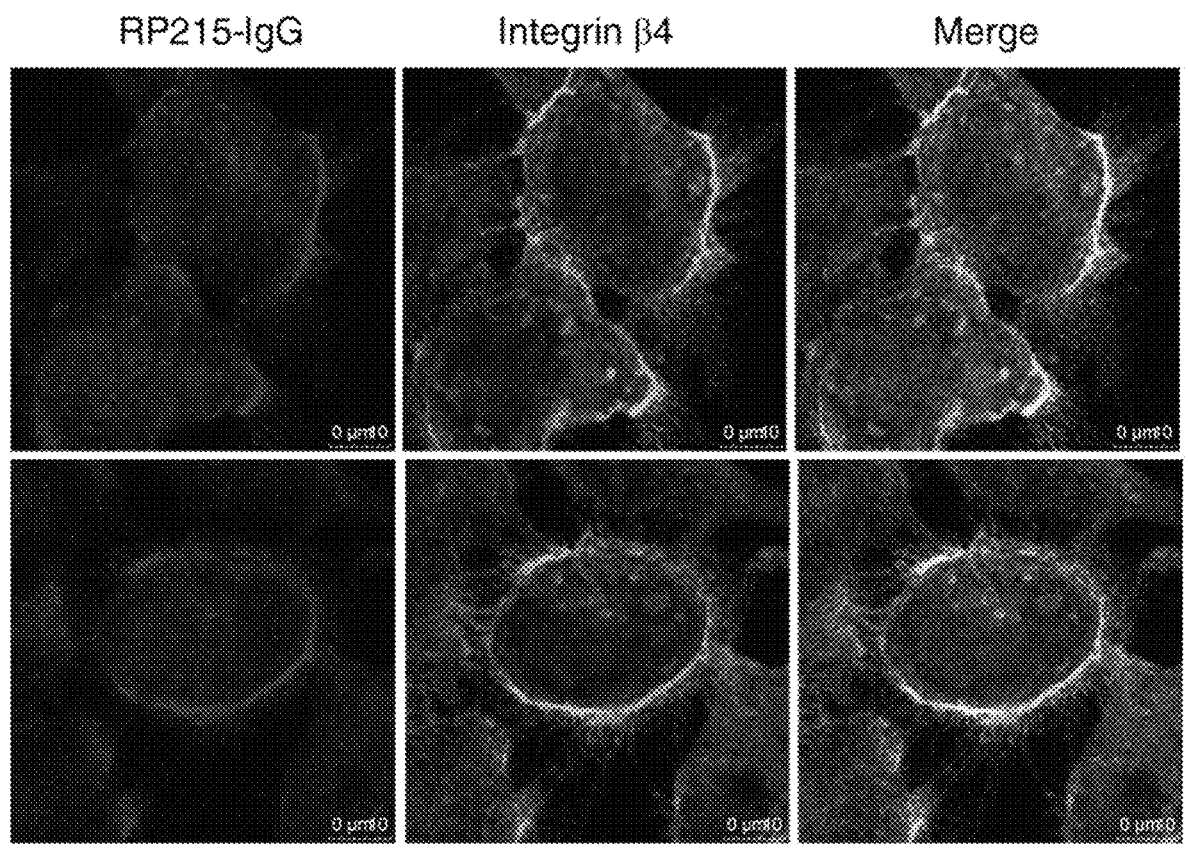
Figures 4, 5, 6, 7, 8, 8B:
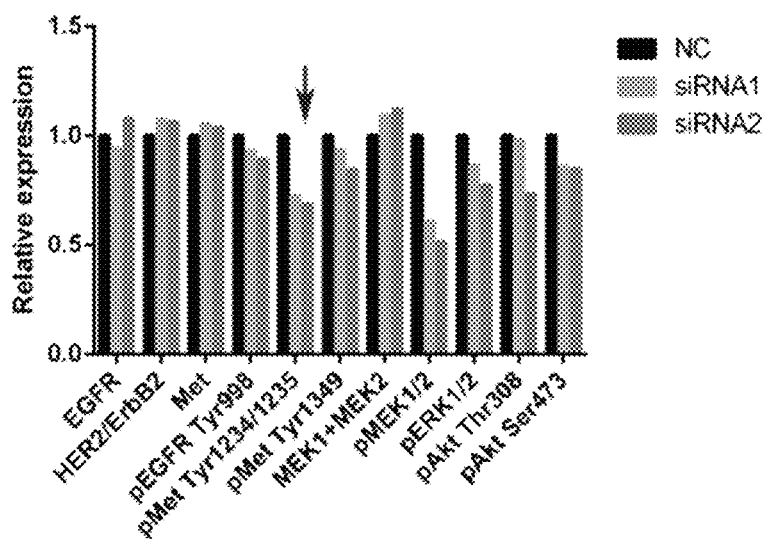
Figures 4, 5, 6, 7, 8, 9, 9A:
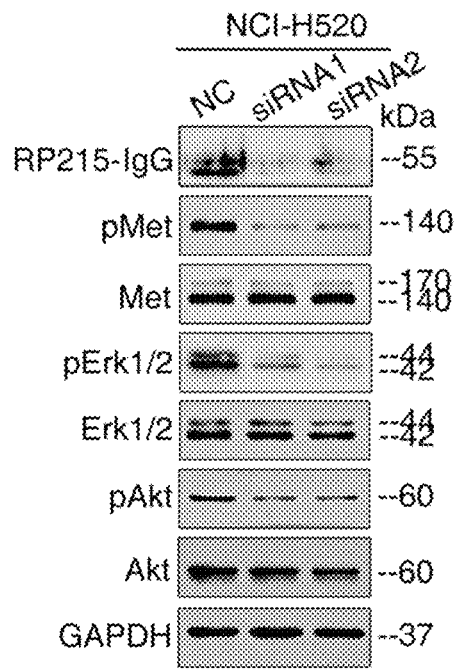
Figures 4, 5, 6, 7, 8, 9, 9B:
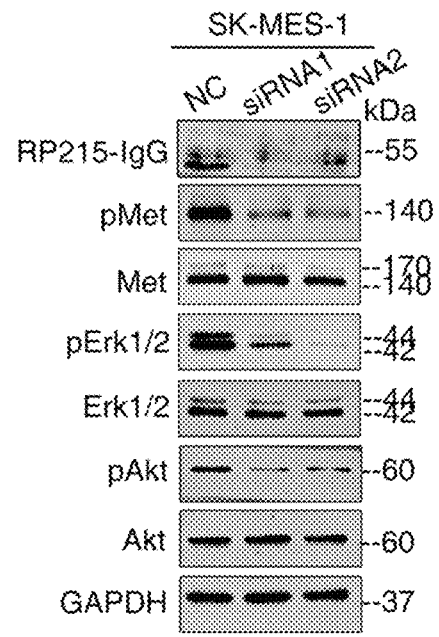
Figures 4, 5, 6, 7, 8, 9, 10, 10A:
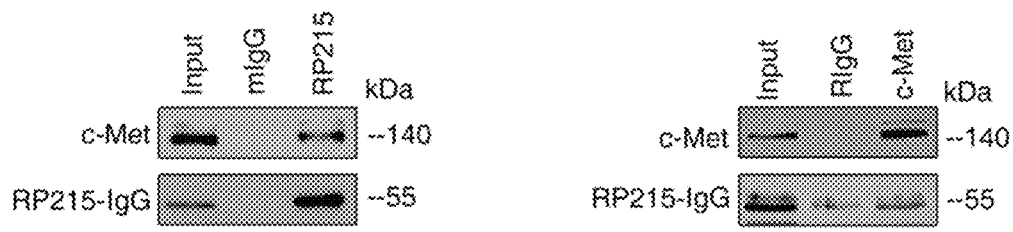
Figures 4, 5, 6, 7, 8, 9, 10, 10B:
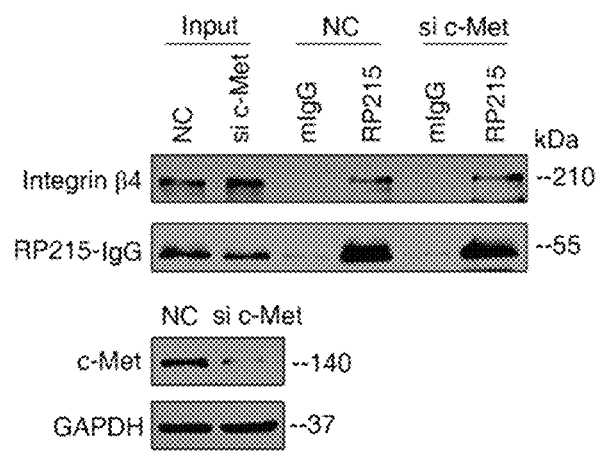
Figures 4, 5, 6, 7, 8, 9, 10, 10C:
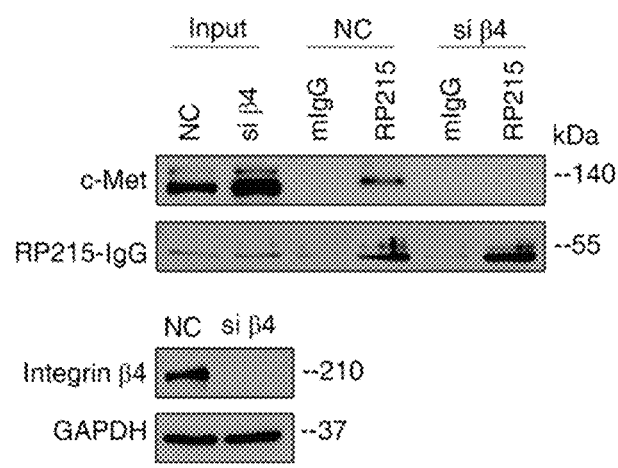
Figures 4, 5, 6, 7, 8, 9, 10, 11, 11A:
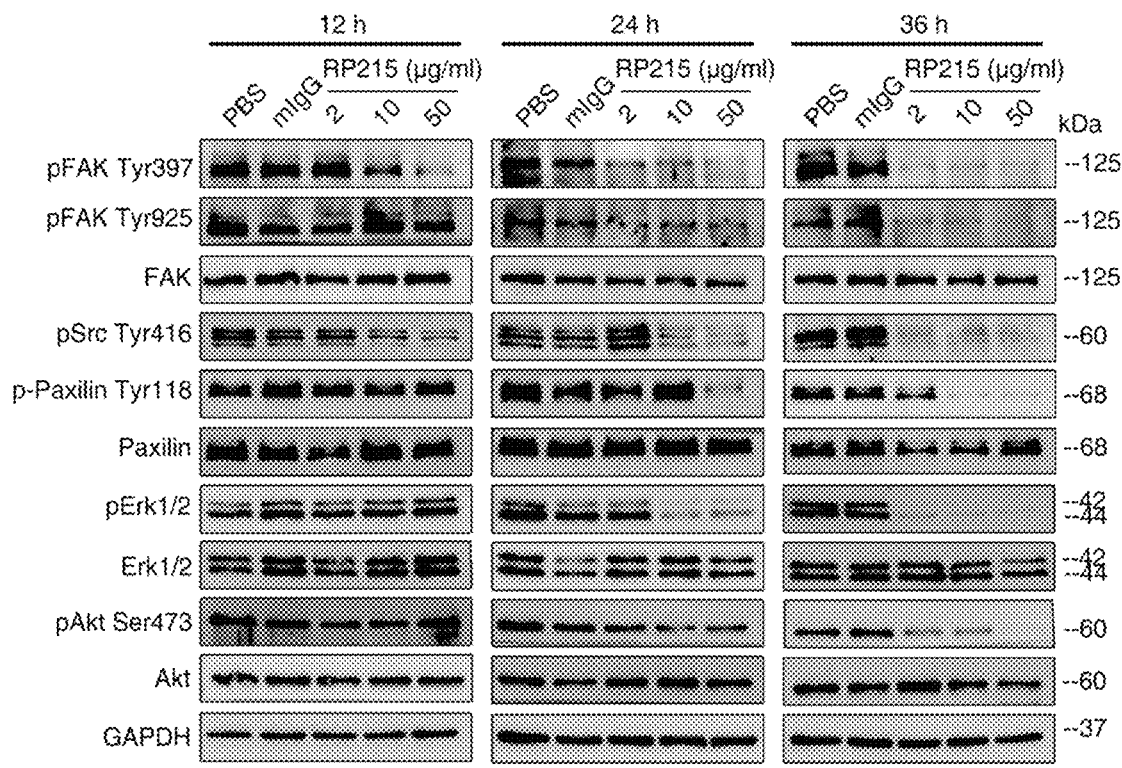
Figures 4, 5, 6, 7, 8, 9, 10, 11, 11B:
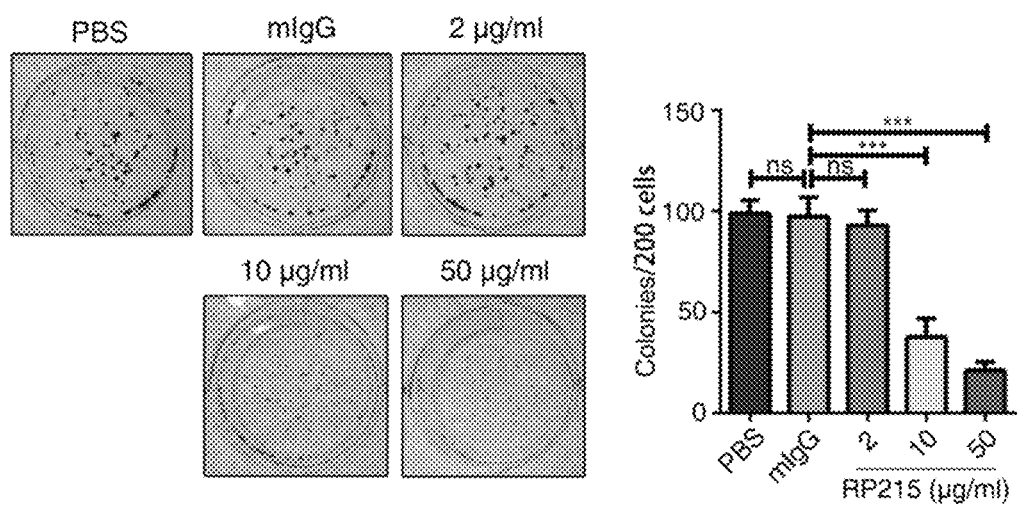
Figures 4, 5, 6, 7, 8, 9, 10, 11, 12, 12A:
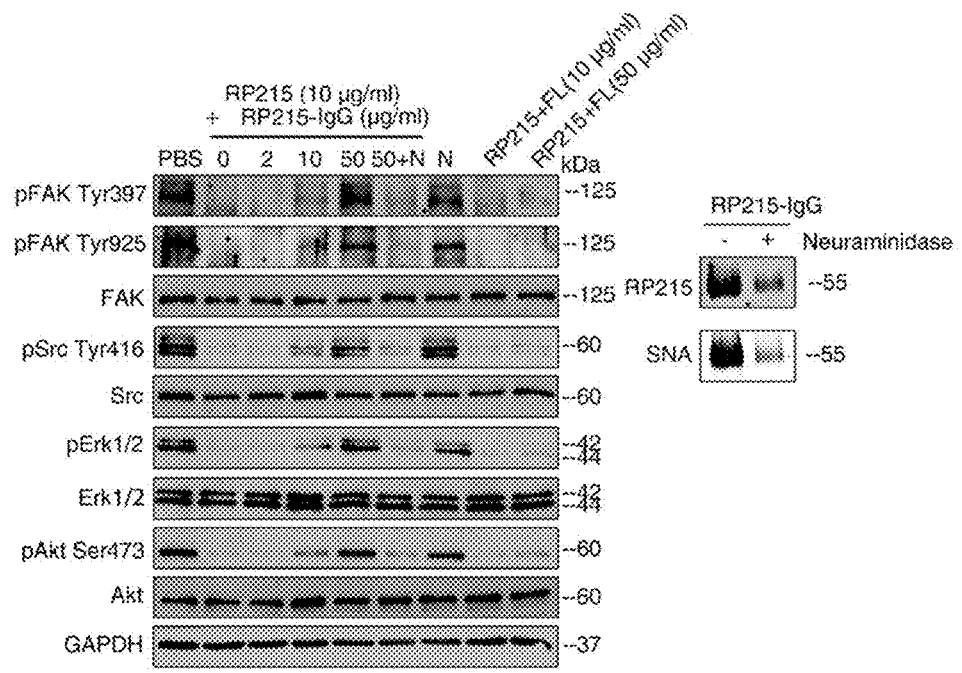
Figures 4, 5, 6, 7, 8, 9, 10, 11, 12, 12B:
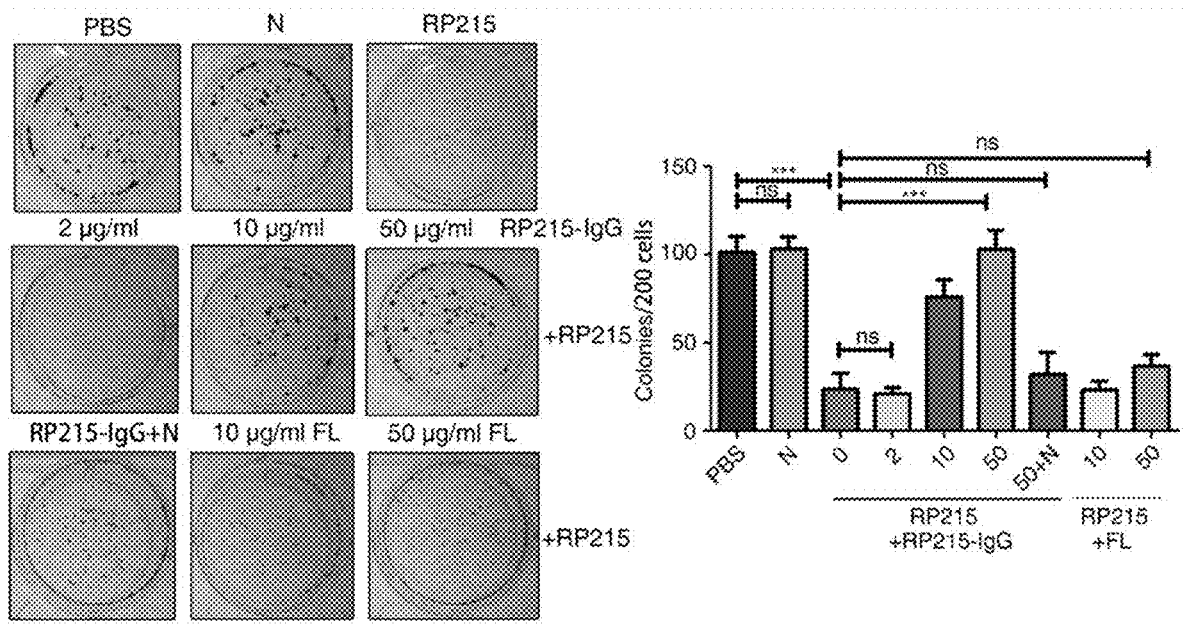
Figure 5A:
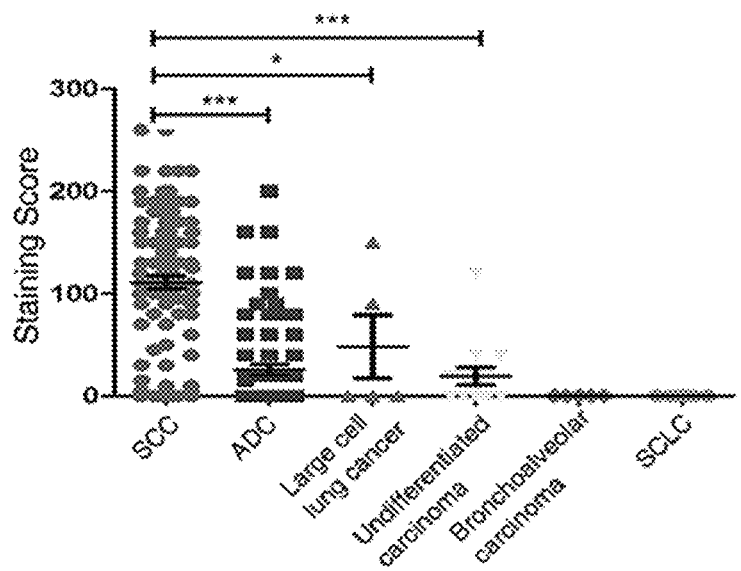
Figure 5B:
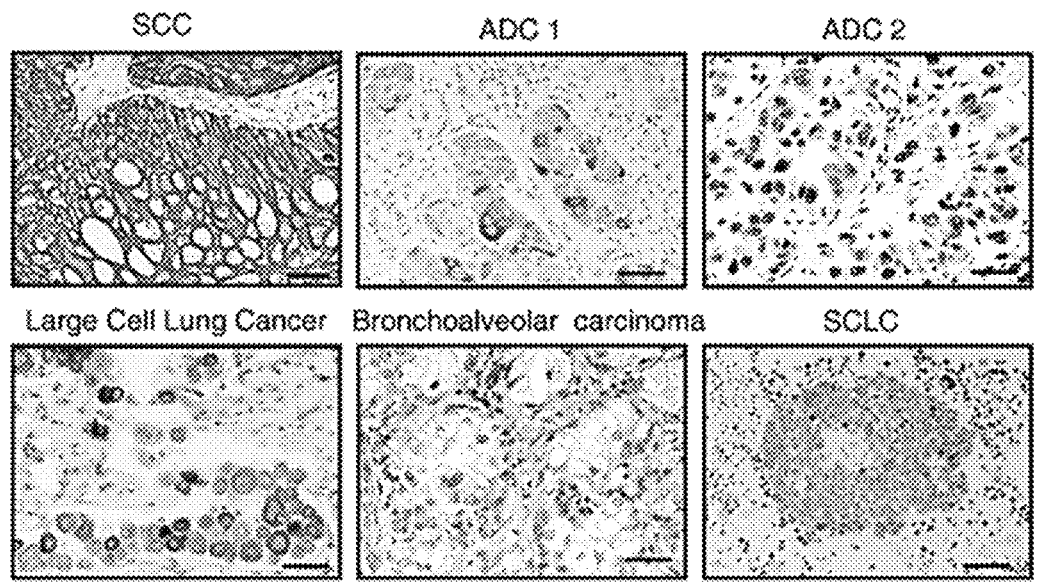
Figure 5C:
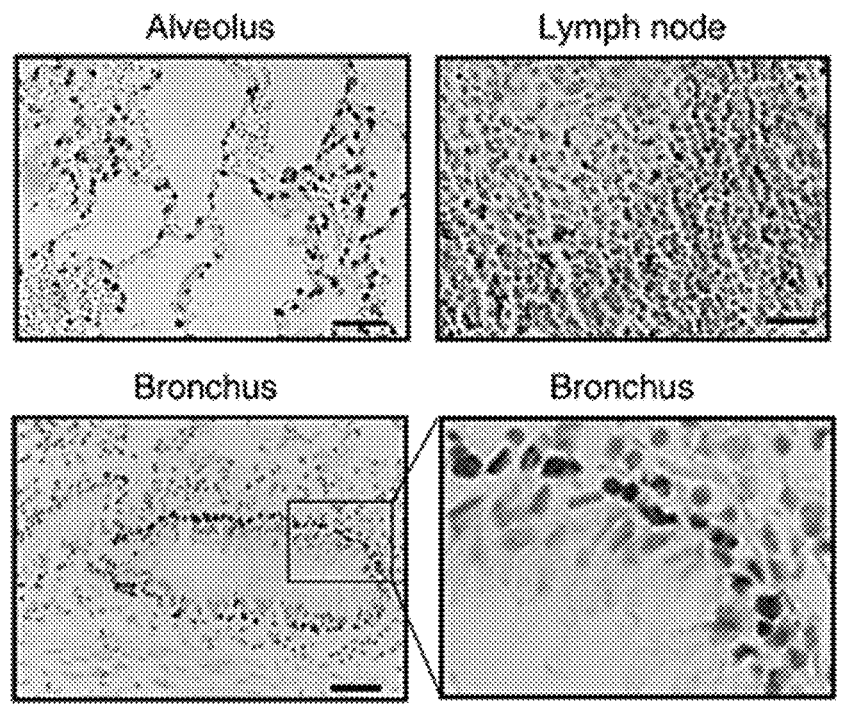
Figure 5D:
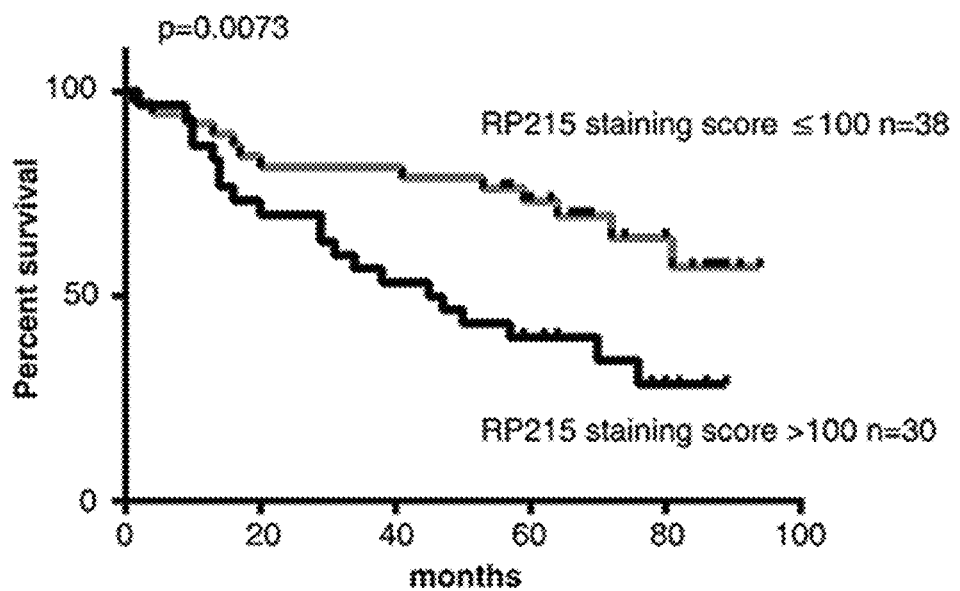
Figure 6A:
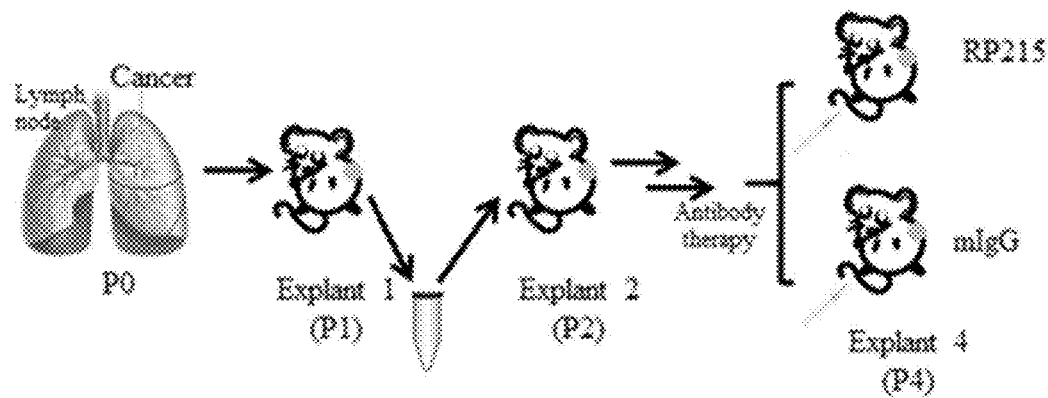
Figure 6B:
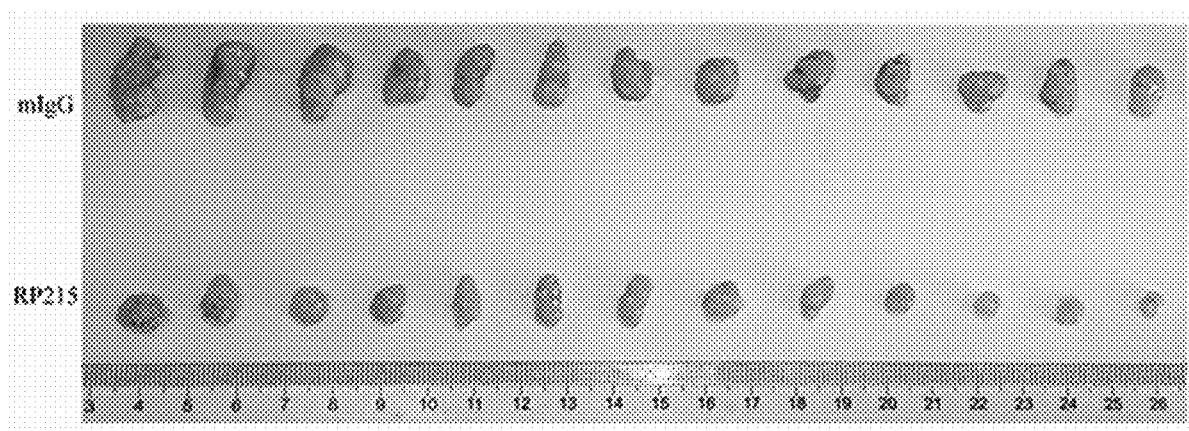
Figure 6C:
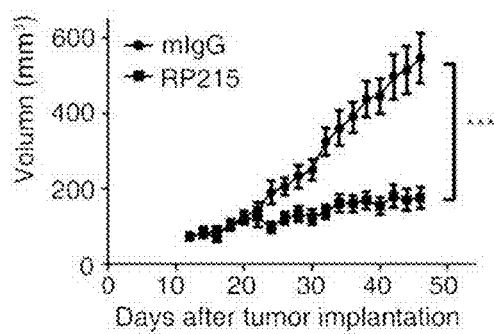
FIG. 6C: Changes of tumor volume with time in the PDX tumor models in Embodiment 7.
Figure 6D:
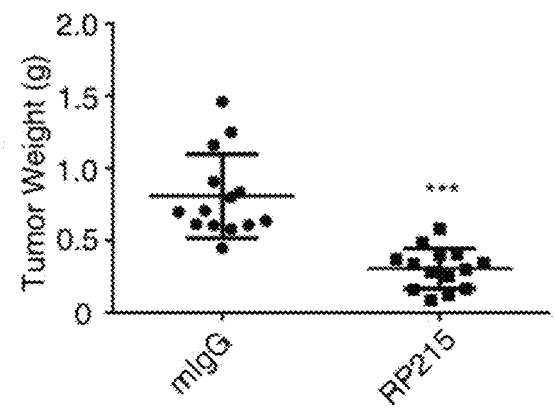
FIG. 6D: Scatter plot and line chart of tumor weight changes in different days in the first group in Embodiment 7.
Figure 6E:
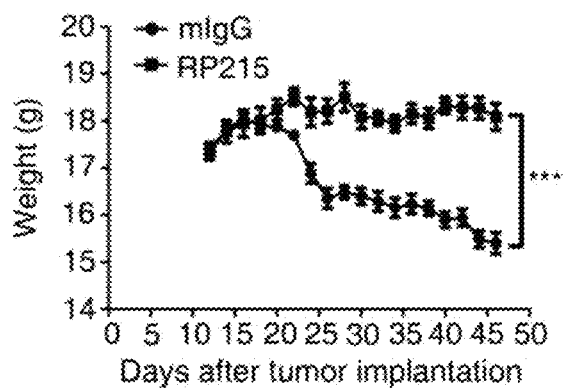
FIG. 6E: Scatter plot and line chart of tumor weight changes in different days in the second group in Embodiment 7.

Subsequently, we explored whether sialylated IgG could be expressed in normal lung tissues. When draining lymph nodes from autopsy (6 cases) or adjacent cancer tissues (23 cases), we found that pseudostratified columnar ciliary epithelial cells, normal alveolar epithelial cells and lymphocytes of draining lymph node were not stained. However, peripheral staining was observed in basal cells of bronchial epithelial cells. So far, LSCC is considered to be derived from this cell population, especially the bronchial hyperplasia basal cells adjacent to the cancer tissue (FIG. 5A-C).

Example 6 Specific Labeling of Other Epithelial Tumors with RP215-IgG

Patient Samples:

Cancer tissue sections included 100 patients with colorectal cancer, 200 patients with breast cancer, 87 patients with prostate cancer, 70 patients with kidney cancer, 45 patients with bladder cancer, 80 patients with salivary gland cystadenocarcinoma, 70 patients with gastric cancer, 20 patients with pancreatic cancer and 50 patients with esophageal cancer; and they were purchased from Shaanxi Chaoying Biotechnology Co., Ltd. and Shanghai Outdo Biotech Co., Ltd. The clinicopathological features were available from the review of medical records. The diagnosis and histological classification of tumor specimens were based on WHO classification. The stage of tumor-lymph node metastasis (TNM) was determined according to the guidelines of the American Joint Committee on Cancer (AJCC).

RP215-IgG was determined in different types of epithelial tumors using monoclonal antibody RP215.

Results showed that the expression frequencies were varied in different cancer tissues: 74% (74/100) in colorectal cancer, 94.5% (189/200) in breast cancer, 85% (74/87) in prostate cancer, 77% (54/70) in kidney cancer, 100% (54/54) in bladder cancer, 94% (75/80) in salivary gland cystadenocarcinoma, 86% (60/70) in gastric cancer, 100% (20/20) in pancreatic cancer and 100% (50/50) in esophageal cancer. Apparently, RP215-IgG was highly expressed in a variety of tumors of epithelial origins.

When draining lymph nodes from autopsy (6 cases) or adjacent cancer tissues (23 cases), we found that pseudostratified columnar ciliary epithelial cells, normal alveolar epithelial cells (left upper corner of FIG. 5C) and lymphocytes of draining lymph node (right upper corner of FIG. 5C) were not stained. However, peripheral staining was observed in basal cells of bronchial epithelial cells (two figures below FIG. 5C). So far, LSCC is considered to be derived from this cell population, especially the bronchial hyperplasia basal cells adjacent to the cancer tissues.

We compared the relationship between expression frequency and tumor metastasis and poor prognosis, and found that the expression level and frequency of RP215-IgG were positively correlated with tumor metastasis and poor prognosis. This suggested that RP215-IgG is involved in the occurrence and metastasis of the above epithelial tumors, with a variety of therapeutic targets for the epithelial tumors, and can be used to predict tumor metastasis and poor prognosis (FIG. 5 D).

Example 7 Treatment of Cancers by Blocking RP215-IgG

Functional Blocking Antibody RP215 Showed Therapeutic Effect in LSCC PDX Models In Vivo The previous experimental results confirmed that the N-glycosyl group at the site Asn162 of $C_H1$ domain of RP215-IgG could be identified by RP215 after modified by sialic acid, and the glycosylation modification of IgG with this functional structure was mediated by sialyltransferase ST3GAL4. The monoclonal antibody RP215 with unique structure was identified to bind RP215-IgG to block its function.

It was involved in the migration and invasion of tumor cells.

Establishment of PDX Tumor Model and Antibody Therapy:

The Beige mice with severe combined immunodeficiency (SCID) were obtained from Vital River Laboratories Technology Co., Ltd. (Beijing, China) at 6 weeks. The animal care and uses were carried out according to the guidelines for animal medication and nursing of the Peking University Health Science Center.

The tumor tissues of 3 patients were obtained from those with lung squamous cell carcinoma who underwent surgical resection at Peking University Cancer Hospital. The fourth generation of PDX was used for antibody therapy. The metastatic tumor was placed in a sterile Petri dish containing RPMI 1640, and then cut into tissue blocks with size of $2 \times 2 \times 2$ mm$^3$. Typically, each segment was implanted into the right and left subcutaneous areas. Antibody therapy was started after the tumor reached around 100 mm$^3$. The mice were randomly assigned to their respective treatment groups. The mIgG or RP215 (dissolved in PBS) was injected via the tail vein at a rate of 5 mg/kg, twice a week, for 6 weeks. The tumor growth condition was monitored every other day.

After understanding the carcinogenic properties of RP215-IgG in LSCC, we detected whether RP215 could establish the therapeutic effects of the PDX models by intravenous injection.

PDX tumors retained most of the key genes expressed in the primary tumor and were closer to the original clinical cancer than the originally established cell line. In our study, we used the tumors of 3 patients with LSCC and the histological analysis of transplanted tumors confirmed that xenografts maintained the LSCC phenotype.

As shown in FIG. 6A-E, compared to the mIgG control, RP215 at a dose of 5 mg/kg per mouse reduced the growth of pre-established tumor by 60%. At the end of the experiment, the average weight of tumors in the RP215 treatment group was $0.31 \pm 0.14$ g, significantly lower than that in the control group ($0.81 \pm 0.29$ g). Similar effects were observed in other two conditions.

Example 8 Production, Quality Control and Preliminary Micro-PET/CT Study of $^{124}$I-PR215

Figure 7A:
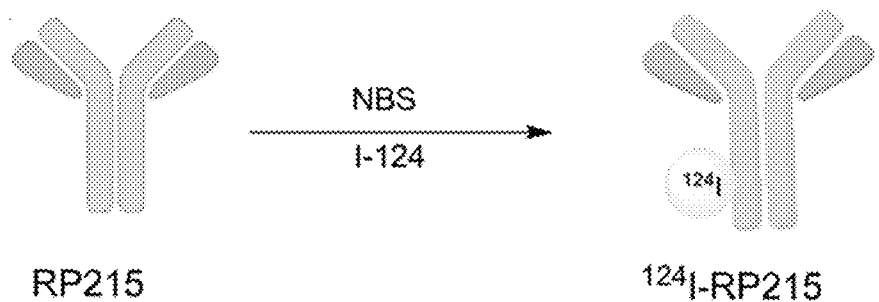
FIG. 7A: Schematic diagram of radiolabeling of $^{124}$I-PR215 in Embodiment 7.

$^{124}$TeO$_2$ (99.0%) was purchased from Center of Molecular Research of Russia, Sumitomo HM-20 cyclotron and $^{124}$I purification system (Industrial Equipment Division) were purchased from Sumitomo Corporation of Japan, radioactivity activity meter was purchased from U.S. Capintec, and Micro-PET/CT was purchased from Mediso Hungary. The schematic diagram of radioactive labels was shown in FIG. 7A.

Labeling and Quality Control:
1. Labeled antibody: PR215, dosage: 0.2 mg, antibody concentration: 2.0 mg/ml.
2. Radioactive$^{124}$I: produced by the cyclotrons of the unit, with batch number of 2018-1-124-003, radioactive concentration: $5 \times 37$ MBq/mL.
3. Purification column: PD-10 column of U.S. Sigma.
4. Oxidizing agent: Bromosuccinimide (abbreviated as NBS), U.S. Sigma.
5. Phosphate buffer solution (abbreviated as PB): 0.1 and 0.01M phosphate buffer solution at pH 7.2 and pH 7.4, prepared by ourselves.
6. Human serum albumin (HSA): content of 10% (diluted with 20% HAS), produced by North China Pharmaceutical Factory.

Experimental instruments: activity meter: (National Institute of Metrology, China), surface contamination meter (Sweden), radioactive iodine-labeled glove box (Shanghai Tongpu Co., Ltd.)

Labeling of Antibody Solution:
7 Take 0.2 mg PR215 (with volume of 200 μL), then add 0.3 ml 0.1M PB at pH 7.4 into it.
8. 0.5 ml of the required radioactive Na$^{124}$I solution was extracted, with a radioactivity of $2.5 \times 37$ MBq, added to the antibody solution to be labeled, and 10 μg of NBS (equivalent to adding 50 μg of NBS per mg of antibody, prepared by 0.01M PBS) was added immediately, after reaction for 60 s, 0.3 ml of 10% HSA was added to terminate the reaction, and then samples were taken to determine the labeling rate, purified and separated through PD-10 column. The volume of upper column: 1.5 mCi, production: 2.0 mCi, radioactivity specific activity: 10 mCi/mg; radioactivity concentration: 1 mCi/mL.
9. Determination of labeling rate: using acetone developing agent. ITLC-SG was used as a stationary phase to carry out uplinking expansion, with the marker at the origin and the free $^{124}$I at the front. The radioactivity count was determined by Radio-TLC, and the labeling rate was calculated.

Figure 7B:
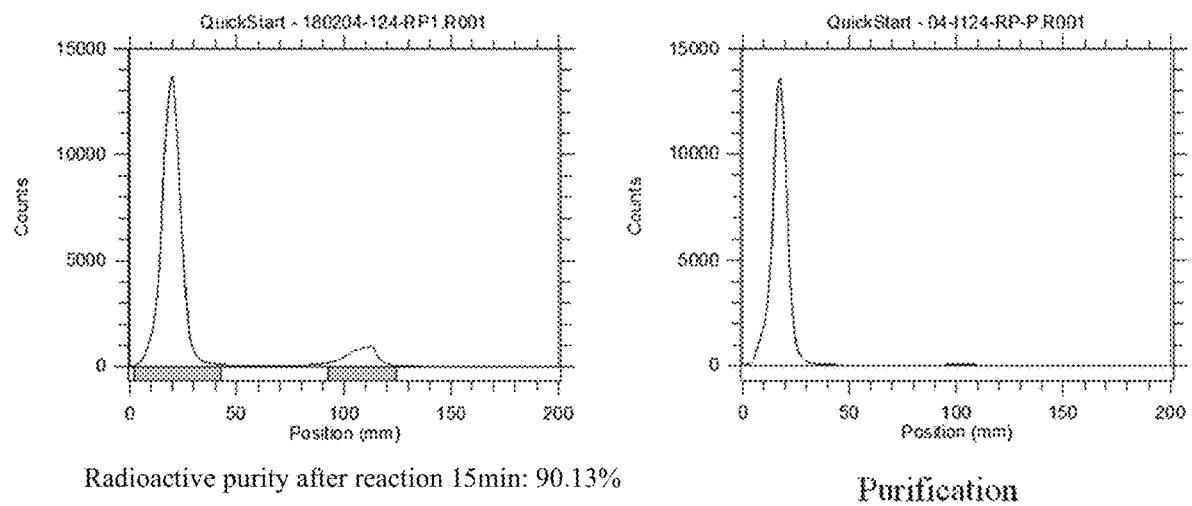
FIG. 7B: Radio-TLC analysis results of $^{124}$I-PR215 before and after labeling and purification in Embodiment 7.

The Radio-TLC analysis of radiolabels before and after purification was shown in FIG. 7B.

Micro-PET Imaging of 24I-PR215

The $^{124}$I-PR215 physiological saline solution of 18.5 MBq was injected into PDX model animals of human lung squamous cell carcinoma via the tail veins. At 20 h, 60 h, 80 h, and 120 h after drug injection, Matrix VIP 3000 animal anesthesia machine was used to anesthetize the mice by blowing 3.0% isoflurane with 300 mL/min of oxygen. The mice were fixed in the prone position on the scanning bed, and maintained in anesthesia state by blowing 1.0-1.5% isoflurane with 150 mL/mi oxygen, and then Micro-PET/CT scan was performed. The scanning energy window was 350-700 KeV, cross-sectional field of view was 80 mm, and the 3D mode acquisition lasted 15 minutes. After the acquisition was completed, the random and scattering attenuation correction was used to reconstruct the 3D images with the Osem algorithm. After the reconstruction, image processing was performed by software MMWKS SUPERARGUS.

Figure 7C:
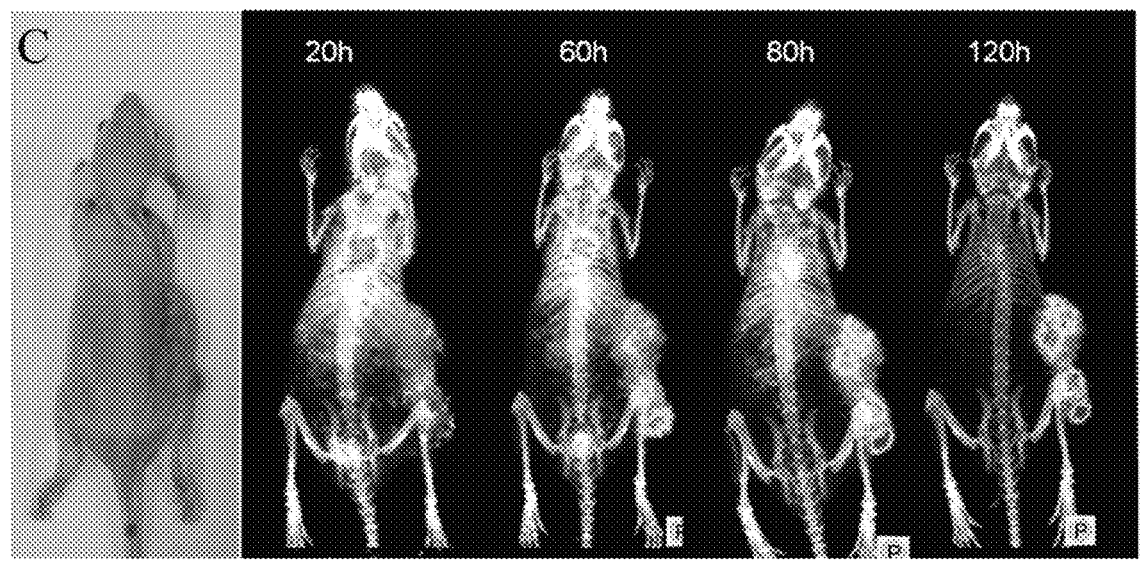
FIG. 7C: Micro-PET/CT imaging of $^{124}$I-PR215 at different times in Embodiment 7.

After the prepared $^{124}$I-PR215 solution was injected into normal mice via tail veins, imaging experiments was conducted by Micro-PET/CT. The results were shown in FIG. 7C. At 20 h, 60 h, 80 h, and 120 h after injection of $^{124}$I-PR215 solution via the tail veins, the radioactive enrichment was significantly enriched from the heart blood pool to the tumor, while radioactivity concentration in other normal tissues and organs was low. In addition, the $^{124}$I was mainly metabolized from the bladder. Micro-PET imaging demonstrated that the $^{124}$I-PR215 prepared in this study conformed to the metabolic behaviors of iodine series monoclonal antibodies in vivo and showed very good radioactive uptake in tumors of model animals.

While the principle and implementation of the present invention are described in the above specific embodiments, those embodiments are only provided to facilitate understanding the core idea of the present invention. It should be noted that, for those of ordinary skill in the art, any obvious modifications, equivalent replacements, or other improvements made without departing from the inventive concept should be included in the scope of protection of the present invention.

What is claimed is:

1. A method of diagnosis of an epithelial tumor expressing a sialylated RP215-IgG, comprising:
   obtaining an epithelial tumor tissue sample from a subject;
   determining the presence of a sialylated RP215-IgG expression pattern in the epithelial tumor tissue using a monoclonal antibody, wherein the monoclonal antibody comprises epitope-specific site binding to a $C_H1$ domain of non-B cell derived IgG comprising the amino acid sequence of SEQ ID NO: 1 with an N-glycosylated sialic acid modification at an Asn162 site of the $C_H1$ domain and is a RP215 monoclonal antibody; and
   predicting metastasis and poor prognosis of the epithelial tumor by detection of the sialylated RP215-IgG in the epithelial tumor tissue sample.

2. A method of treatment of an epithelial tumor expressing a sialylated RP215-IgG, comprising: administering a blocking antibody to an epithelial tumor, wherein
   the epithelial tumor expresses a sialylated RP215-IgG protein and
   the expressed sialylated RP215-IgG protein is a $C_H1$ domain of non-B cell derived IgG comprising the amino acid sequence of SEQ ID NO: 1 with an N-glycosylated sialic acid modification at an Asn162 site of the $C_H1$ domain and is a ligand of integrin α6β4, and wherein the blocking antibody has epitope-specific site binding to a $C_H1$ domain of non-B cell derived IgG comprising the amino acid sequence of SEQ ID NO: 1 with an N-glycosylated sialic acid modification at an Asn162 site of the $C_H1$ domain, and blocks the function of activating an α6β4-FAK-c-Met signaling pathway in the epithelial tumor when the expressed sialylated RP215-IgG protein binds to the integrin α6β4 and is a RP215 monoclonal antibody.

3. The method of diagnosis according to claim 1, wherein the epithelial tumor is selected from the group consisting of non-small cell lung cancer, intestinal cancer, breast cancer, prostate cancer, kidney cancer, bladder cancer, saliva gland cystadenocarcinoma, gastric cancer, squamous cell carcinoma, pancreatic cancer and esophageal cancer.

4. The method of treatment according to claim 2 wherein the epithelial tumor is selected from the group consisting of non-small cell lung cancer, intestinal cancer, breast cancer, prostate cancer, kidney cancer, bladder cancer, saliva gland cystadenocarcinoma, gastric cancer, squamous cell carcinoma, pancreatic cancer and esophageal cancer.

* * * * *

SEQUENCE LISTING

<160> NUMBER OF SEQ ID NOS: 4

<210> SEQ ID NO 1
<211> LENGTH: 170
<212> TYPE: PRT
<213> ORGANISM: Homo sapiens

<400> SEQUENCE: 1

Lys Asp Tyr Phe Pro Glu Pro Val Thr Val Ser Trp Asn Ser Gly Ala
1               5                   10                  15

Leu Thr Ser Gly Val His Thr Phe Pro Ala Val Leu Gln Ser Ser Gly
            20                  25                  30

Leu Tyr Ser Leu Ser Ser Val Val Thr Val Pro Ser Ser Asn Phe Gly
        35                  40                  45

Thr Gln Thr Tyr Thr Cys Asn Val Asp His Lys Pro Ser Asn Thr Lys
    50                  55                  60

Val Asp Lys Thr Val Glu Arg Lys Cys Cys Val Glu Cys Pro Pro Cys
65                  70                  75                  80

Pro Ala Pro Pro Val Ala Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Gln Phe Asn Trp Tyr
        115                 120                 125

Val Asp Gly Val Glu Val His Asn Ala Lys Thr Lys Pro Arg Glu Glu
    130                 135                 140

Gln Phe Asn Ser Thr Phe Arg Val Val Ser Val Leu Thr Val Val His
145                 150                 155                 160

Gln Asp Trp Leu Asn Gly Lys Glu Tyr Lys
                165                 170

<210> SEQ ID NO 2
<211> LENGTH: 170
<212> TYPE: PRT
<213> ORGANISM: Homo sapiens

<400> SEQUENCE: 2

Lys Asp Tyr Phe Pro Glu Pro Val Thr Val Ser Trp Asn Ser Gly Ala
1               5                   10                  15

Leu Thr Ser Gly Val His Thr Phe Pro Ala Val Leu Gln Ser Ser Gly
            20                  25                  30

Leu Tyr Ser Leu Ser Ser Val Val Thr Val Pro Ser Ser Asn Phe Gly
        35                  40                  45

Thr Gln Thr Tyr Thr Cys Asn Val Asp His Lys Pro Ser Asn Thr Lys
    50                  55                  60

Val Asp Lys Thr Val Glu Arg Lys Cys Cys Val Glu Cys Pro Pro Cys
65                  70                  75                  80

Pro Ala Pro Pro Val Ala Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Gln Phe Asn Trp Tyr
        115                 120                 125

Val Asp Gly Val Glu Val His Asn Ala Lys Thr Lys Pro Arg Glu Glu
    130                 135                 140

Asn Phe Asn Ser Thr Phe Arg Val Val Ser Val Leu Thr Val Val His

```
                        145                 150                 155                 160
Gln Asp Trp Leu Asn Gly Lys Glu Tyr Lys
                165                 170

<210> SEQ ID NO 3
<211> LENGTH: 170
<212> TYPE: PRT
<213> ORGANISM: Homo sapiens

<400> SEQUENCE: 3

Lys Asp Tyr Phe Pro Glu Pro Val Thr Val Ser Trp Asn Ser Gly Ala
1               5                   10                  15

Leu Thr Ser Gly Val His Thr Phe Pro Ala Val Leu Gln Ser Ser Gly
                20                  25                  30

Leu Tyr Ser Leu Ser Ser Val Val Thr Val Pro Ser Ser Asn Phe Gly
            35                  40                  45

Thr Gln Thr Tyr Thr Cys Asn Val Asp His Lys Pro Ser Asn Thr Lys
        50                  55                  60

Val Asp Lys Thr Val Glu Arg Lys Cys Cys Val Glu Cys Pro Pro Cys
65                  70                  75                  80

Pro Ala Pro Pro Val Ala Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Gln Phe Asn Trp Tyr
        115                 120                 125

Val Asp Gly Val Glu Val His Asn Ala Lys Thr Lys Pro Arg Glu Glu
    130                 135                 140

Gln Phe Asn Ser Thr Phe Arg Val Val Ser Val Leu Thr Val Val His
145                 150                 155                 160

Gln Asp Trp Leu Asn Gly Lys Glu Tyr Lys
                165                 170

<210> SEQ ID NO 4
<211> LENGTH: 9
<212> TYPE: PRT
<213> ORGANISM: Homo sapiens

<400> SEQUENCE: 4

Thr Val Ser Trp Asn Ser Gly Ala Leu
1               5
```